United States Patent
McManus et al.

(10) Patent No.: US 10,989,716 B2
(45) Date of Patent: Apr. 27, 2021

(54) BIOMARKERS FOR THE DETECTION OF ACUTE REJECTION IN HEART TRANSPLANTATION

(71) Applicant: The University of British Columbia, Vancouver (CA)

(72) Inventors: Bruce McManus, Delta (CA); Raymond Ng, Vancouver (CA); Scott Tebbutt, Vancouver (CA); Janet Wilson-McManus, Delta (CA); Zsuzsanna Hollander, Vancouver (CA); Karen Lam, Vancouver (CA); Virginia Chen, Vancouver (CA); Darlene Dai, Surrey (CA); Casey Shannon, Vancouver (CA); Andrew Ignaszewski, Vancouver (CA); Robert Balshaw, Winnipeg (CA); Robert McMaster, Vancouver (CA); Paul Keown, Delta (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 15/571,019

(22) PCT Filed: Apr. 28, 2016

(86) PCT No.: PCT/IB2016/052402
§ 371 (c)(1),
(2) Date: Oct. 31, 2017

(87) PCT Pub. No.: WO2016/178121
PCT Pub. Date: Nov. 10, 2016

(65) Prior Publication Data
US 2018/0164326 A1    Jun. 14, 2018

Related U.S. Application Data

(60) Provisional application No. 62/156,134, filed on May 1, 2015.

(51) Int. Cl.
| | | |
|---|---|---|
| *C12Q 1/68* | (2018.01) | |
| *G01N 33/68* | (2006.01) | |
| *C12Q 1/6883* | (2018.01) | |
| *G01N 33/50* | (2006.01) | |

(52) U.S. Cl.
CPC ....... *G01N 33/6893* (2013.01); *C12Q 1/6883* (2013.01); *G01N 33/5091* (2013.01); *G01N 33/6887* (2013.01); *C12Q 2600/158* (2013.01); *G01N 2800/245* (2013.01); *G01N 2800/325* (2013.01); *G01N 2800/50* (2013.01); *G01N 2800/52* (2013.01)

(58) Field of Classification Search
CPC ........... G01N 33/5091; G01N 33/6893; G01N 2800/325; G01N 33/6887; C12Q 1/6883
See application file for complete search history.

(56) References Cited

FOREIGN PATENT DOCUMENTS

| | | |
|---|---|---|
| WO | 2009124402 | 10/2009 |
| WO | 2009124404 | 10/2009 |
| WO | 2016178121 | 11/2016 |

OTHER PUBLICATIONS

Cohen Freue et al., "Computational Biomarker Pipeline from Discovery to Clinical Implementation: Plasma Proteomic Biomarkers for Cardiac Transplantation", PLoS Computational Biology, vol. 9, No. 4, Apr. 4, 2013, pp. 1-15.
EP16789373.4, "Extended European Search Report", dated Aug. 9, 2018, 9 pages.
Kasamatsu et al., "Identification of Candidate Genes Associated with Salivary Adenoid Cystic Carcinomas Using Combined Comparative Genomic Hybridization and Oligonucleotide Microarray Analyses", The International Journal of Biochemistry & Cell Biology, vol. 37, No. 9, Sep. 1, 2005, pp. 1869-1880.
Lin et al., "Whole Blood Genomic Biomarkers of Acute Cardiac Allograft Rejection", The Journal of Heart and Lung Transplantation, vol. 28, No. 9, Sep. 1, 2009, pp. 927-935.
Thach et al., "Surveillance of Transcriptomes in Basic Military Trainees with Normal, Febrile Respiratory Illness, and Convalescent Phenotypes", Genes & Immunity, vol. 6, No. 2, Oct. 1, 2005, pp. 588-595.
International Search Report and Written Opinion from International Application No. PCT/IB2016/052402, dated Jul. 21, 2016, 18 pages.
Deng et al., "Noninvasive discrimination of rejection in cardiac allograft recipients using gene expression profiling.", American Journal of Transplantation, vol. 6(1), Jan. 2006, pp. 150-160.
Hollander et al., Transplantation, vol. 90(12), 2010, pp. 1388-1393.
Holweg et al., "Identification and classification of acute cardiac rejection by intragraft transcriptional profiling.", Circulation, vol. 123(20), May 24, 2011, pp. 2236-2243.
Khatri et al., "A common rejection module (CRM) for acute rejection across multiple organs identifies novel therapeutics for organ transplantation", Journal of Experimental Medicine, vol. 210(11), Oct. 14, 2013, pp. 2205-2221.
Morgun et al., "Molecular Profiling Improves Diagnoses of Rejection and Infection in Transplanted Organs", Circulation Research, vol. 98(12), May 25, 2006, pp. 74-83.
PCT/IB2016/052402, "International Preliminary Report on Patentability", dated Nov. 16, 2017, 12 pages.
PCT/IB2016/052402, "International Search Report and Written Opinion", dated Jul. 21, 2016, 18 pages.
EP16789373.4, "Summons to Attend Oral Proceedings", Jun. 9, 2020, 8 pages.

*Primary Examiner* — Robert C Hayes
(74) *Attorney, Agent, or Firm* — Kilpatrick Townsend & Stockton LLP

(57) ABSTRACT

The present disclosure relates to methods of diagnosing acute rejection of a cardiac allograft in a subject using genomic expression profiling, proteomic expression profiling, or both on panels of nucleic acid markers and proteomic markers.

4 Claims, 2 Drawing Sheets

BIOMARKERS FOR THE DETECTION OF ACUTE REJECTION IN HEART TRANSPLANTATION

CROSS-REFERENCE TO RELATED APPLICATIONS

This application claims priority to U.S. Provisional Application No. 62/156,134, filed May 1, 2015, titled "BIOMARKERS FOR THE DETECTION OF ACUTE REJECTION IN HEART TRANSPLANTATION", the disclosure of which is incorporated herein by reference in its entirety.

BACKGROUND OF THE INVENTION

Transplantation is considered the primary therapy for patients with end-stage vital organ failure. While the availability of immunosuppressants such as cyclosporine and Tacrolimus has improved allograft recipient, e.g., heart transplant recipient, survival and wellbeing, identification of rejection of the allograft as early and as accurately as possible, and effective monitoring and adjusting immunosuppressive medication doses is still of primary importance to the continuing survival of the allograft recipient.

Rejection of an allograft may be generally described as the result of recipient's immune response to nonself antigens expressed by the donor tissues. Acute rejection may occur within days or weeks of the transplant, while chronic rejection may be a slower process, occurring months or years following the transplant.

At present, invasive biopsies, such as endomyocardial, liver core, and renal fine-needle aspiration biopsies, are widely regarded as the gold standard for the surveillance and diagnosis of allograft rejections, but are invasive procedures which carry risks of their own (e.g. Mehra M R, et al. Curr. Opin. Cardiol. 2002 March; 17(2): 131-136.). Biopsy results may also be subject to reproducibility and interpretation issues due to sampling errors and inter-observer variabilities, despite the availability of international guidelines such as the Banff schema for grading liver allograft rejection (Ormonde et al 1999. Liver Transplantation 5:261-268) or the Revised ISHLT transplantation scale (Stewart et al. 2005. J Heart Lung Transplant, 2005; 24: 1710-20). Although less invasive (imaging) techniques have been developed such as angiography and IVUS for monitoring chronic heart rejection, these alternatives are also susceptible to limitations similar to those associated with biopsies.

The severity of allograft rejection as determined by biopsy may be graded to provide standardized reference indicia. The International Society for Heart and Lung Transplantation scale (ISHLT) provides a means of grading biopsy samples for heart transplant subjects (Table 1)

TABLE 1

International Society for Heart and Lung Transplantation grading of heart transplant rejection for histopathologic biopsy analysis.

| Grade | Comment |
| --- | --- |
| 0R | No acute cellular rejection: No evidence of mononuclear inflammation or myocyte damage or necrosis. |
| 1R | Mild, low-grade, acute cellular rejection: Mononuclear cells are present and there may be limited myocyte damage and necrosis. |
| 2R | Moderate, intermediate-grade, acute cellular rejection: Two or more foci of mononuclear cells with associated myocyte damage and necrosis are present. The damage may be found in the same biopsy, or two separate biopsies. Eosinophils may be present. |
| 3R | Severe, high-grade, acute cellular rejection: Widespread, diffuse myocyte damage and necrosis, and disruption of normal architecture across several biopsies. Edema, interstitial hemorrhage and vasculitis may be present. The infiltrate may be polymorphous. |

Indicators of allograft rejection may include a heightened and localized immune response as indicated by one or more of localized or systemic inflammation, tissue injury, allograft infiltration of immune cells, altered composition and concentration of tissue- and blood-derived proteins, differential oxygenation of allograft tissue, edema, thickening of the endothelium, increased collagen content, altered intramyocardial blood flow, infection, necrosis of the allograft and/or surrounding tissue, and the like.

Allograft rejection maybe described as 'acute' or 'chronic'. Acute rejection is generally considered to be rejection of a tissue or organ allograft within ~6 months of the subject receiving the allograft. Acute rejection may be characterized by cellular and humoral insults on the donor tissue, leading to rapid graft dysfunction and failure of the tissue or organ. Chronic rejection is generally considered to be reject of a tissue or organ allograft beyond 6 months, and may be several years after receiving the allograft. Chronic rejection may be characterized by progressive tissue remodeling triggered by the alloimmune response may lead to gradual neointimal formation within arteries, contributing to obliterative vasculopathy, parenchymal fibrosis and consequently, failure and loss of the graft. Depending on the nature and severity of the rejection, there may be overlap in the indicators or clinical variables observed in a subject undergoing, or suspected of undergoing, allograft rejection—either chronic or acute.

Attempts have been made to reduce the number of biopsies per patient, but may be generally unsuccessful, due in part to the difficulty in pinpointing the sites where rejection starts or progresses, and also to the difficulty in assessing tissue without performing the actual biopsy. Noninvasive surveillance techniques have been investigated, and may provide a reasonable negative prediction of allograft rejection, but may be of less practical utility in a clinical setting (Mehra et al., supra).

The scientific and patent literature is replete with reports of this marker or that being important for identification/diagnosis/prediction/treatment of every medical condition that can be named. Even within the field of allograft rejection, a myriad of markers are recited (frequently singly), and conflicting results may be presented. This conflict in the literature, added to the complexity of the genome (estimates range upwards of 30,000 transcriptional units), the variety of cell types (estimates range upwards of 200), organs and tissues, and expressed proteins or polypeptides (estimates range upwards of 80,000) in the human body, renders the number of possible nucleic acid sequences, genes, proteins or combinations thereof useful for diagnosing acute organ rejection is staggering. Variation between individuals presents additional obstacles, as well as the dynamic range of protein concentration in plasma (ranging from $10^{-6}$ to $10^3$ micro g/mL) with many of the proteins of potential interest existing at very low concentrations) and the overwhelming quantities of the few, most abundant plasma proteins (constituting ~99 percent of the total protein mass.

The CARGO study (Cardiac Allograft Rejection Gene Expression Observation) (Deng et al., 2006. Am J. Transplantation 6:150-160) used custom microarray analysis of—7300 genes and RT-PCR to examine gene expression profile in subjects exhibiting an ISHLT score of 3 A or greater in samples taken 6 months or more post-transplant.

Immune cells that have a role in recognizing may be useful as indicators of allograft rejection. WO 2005/05721 describes methods for distinguishing immunoreactive T-lymphocytes that bind specifically to donor antigen presenting cells, providing a population of T-lymphocytes that are specifically immunoreactive to the donor antigens. Again however, particular markers that may be useful in assessing or diagnosing allograft rejection remain to be determined.

Traum et al., 2005 (Pediatr. Transplant 9(6):700-711) provides a general overview of transplantation proteomics. Exploration of biomarkers directly in the plasma proteome presents two main challenges—the dynamic range of protein concentrations extends from 10"6 to 103 micro g/mL (Anderson et al. 2004. MoI Cell Proteomics 3:311-326), with many of the proteins of potential interest existing at very low concentrations and the most abundant plasma proteins comprising as much as 99 percent of the total protein mass.

Maintenance or measurement of B2M serum levels in heart transplant patients was suggested as helpful in managing long-term immunosuppressive therapy (Erez et al., 1998. J Heart Lung Transplant 17:538-541). PCT Publication WO 2009/003142 disclose that B2M, along with another protein may be useful as biomarkers for peripheral artery disease.

Borozdenkova et al. 2004 (J. Proteome Research 3:282-288) discloses that alpha B-crystallin and tropmyosin were elevated in a set of cardiac transplant subjects.

Ishihara, 2008 (J. MoI Cell Cardiology 45:S33) discloses that ADIPOQ may have a role in cardiac transplantation, and Nakano (Transplant Immunology 2007 17:130-136) suggests that upregulation of ADIPOQ may be necessary for overcoming rejection in liver transplant subjects.

Antibodies that bind SHBG (PCT Publication WO 2007/024715) and F10 (PCT Publication WO 2005/020927) are suggested as being useful in preventing graft rejection.

SERPINF1 and C1Q are disclosed as biomarkers associated with an increased risk of a cardiovascular event; the biomarkers maybe detected in a sample of an atherosclerotic plaque from a subject (PCT Publication WO 2009/017405); sequences for SERPINF1 may also be useful in an assay to select optimal blood vessel graft (US Publication 2006/0003338).

Complement is also known to have a role in rejection of allografts—Csencits et al., 2008 (Am J. Transplantation 8:1622-1630) summarizes past studies on various complement components and observes an accelerated humoral immune response in C1Q-/- mice allograft recipients.

PCT Publications WO2006/083986, WO206/122407, US Publications 2008/0153092, 2006/0141493 and U.S. Pat. No. 7,235,358 disclose methods for using panels of biomarkers (proteomic or genomic) for diagnosing or detecting various disease states ranging from cancer to organ transplantation Alakulppi et al, 2007 (Transplantation 83:791-798) discloses the diagnosis of acute renal allograft rejection using RT-PCR for eight markers.

A review by Fildes et al 2008 (Transplant Immunology 19:1-11) discusses the role of cell types in immune processes following lung transplantation, and discloses that AICL (CLEC2B) interaction with NK cell proteins may have a role in acute and chronic rejection Integration of multiple platforms (proteomics, genomics) has been suggested for diagnosis and monitoring of various cancers, however discordance between protein and mRNA expression is identified in the field (Chen et al., 2002. Mol Cell Proteomics 1:304-313; Nishizuka et al., 2003 Cancer Research 63:5243-5250). Previous studies have reported low correlations between genomic and proteomic data (Gygi S P et al. 1999. Mol Cell Biol.\9?12Q-\730; Huber et al., 2004 Mol Cell Proteomics 3:43-55).

BRIEF SUMMARY OF THE INVENTION

The present disclosure relates to methods of diagnosing acute rejection of a cardiac allograft, e.g. a heart transplant, using genomic expression profiling, and/or proteomic expression profiling on panels of nucleic acid markers and/or proteomic markers.

In a first aspect, the disclosure provides a method of diagnosing the acute rejection status of a heart transplant using a biomarker panel comprising one or more nucleic acid markers, the method comprising the steps of: determining the nucleic acid expression profile of the one or more nucleic acid markers in a biological sample from the subject, the nucleic acid markers selected from the group consisting of the nucleic acid markers in Table 3; comparing the nucleic acid expression profile to a control profile; determining whether expression of the one or more nucleic acid markers is increased or decreased relative to the control profile, wherein the increase or decrease of the one or more than one nucleic acid markers is indicative of the acute rejection status of the subject. In some embodiments, the biomarker panel comprises at least two, at least three, at least four, at least five, at least six, at least ten, at least fifteen, at least twenty nucleic acid markers selected from Table 3. In one embodiment, the biomarker panel comprises or consists of all the nucleic acid markers in Table 5. In another embodiment, the biomarker panel comprises or consists of all the nucleic acid markers in Table 7.

In a second aspect, the disclosure provides a method of determining the acute rejection status in heart transplant of a subject using a biomarker panel comprising one or more proteomic markers, the method comprising the steps of: determining the proteomic expression profile of the one or more proteomic markers, e.g., two, three, four, five, or six proteomic markers, in a biological sample from the subject, the proteomic markers selected from the group comprising of the proteomic markers in Table 4; comparing the proteomic expression profile of to a control profile; determining whether expression of the one or more proteomic markers is increased or decreased relative to the control profile; wherein the increase or decrease of the one or more than one proteomic markers is indicative of the acute rejection status of the subject. In one embodiment, the biomarker panel comprises all proteomic markers in Table 4.

In a third aspect, a method of determining the acute rejection status of a heart transplant in a subject using a biomarker panel comprising one or more nucleic acid marker and one or more proteomic markers is provided. The method comprises the steps of: determining the nucleic acid expression profile of one or more nucleic acid markers, e.g., at least two, at least three, at least four, at least five, at least six, at least ten, at least fifteen, or at least twenty nucleic acid markers in a biological sample from the subject, the nucleic acid markers selected from the group comprising the nucleic acid markers in Table 3; comparing the nucleic acid expression profile of the one or more than one nucleic acid markers to a control profile; determining the proteomic expression profile of one or more proteomic markers, e.g., two, three, four, five, or six proteomic markers, in a biological sample from the subject, the proteomic markers selected from the group comprising of the proteomic markers in Table 4; comparing the proteomic expression profile of the one or more than one proteomic markers to a control profile; determining whether the expression level of the one or more nucleic acid markers, and one or more proteomic markers is increased or decreased relative to the control profile; wherein the increase or decrease of the one or more than one nucleic acid markers or the increase or decrease of the one or more proteomic markers is indicative of the acute rejection status of the subject.

In some embodiments, the nucleic acid expression profile is determined by PCR, HTG EdgeSeq or Nano String nCounter and the proteomic expression profile is determined by an immunoassay.

In some embodiments, the biomarker panel has an AUC of at least 0.6, and/or a sensitivity of at least 80%, and/or a specificity of at least 15%, and/or a positive predictive value (PPV) of at least 4%, and/or a negative predictive value (NPV) of at least 98%, in predicting the status of acute rejection of heart transplant. In some embodiments, the assays using the biomarker panel described herein show comparable performance (e.g., NPV and PPV) to commercially available tests, such as the AlloMap assay by CareDx. In some embodiments, the assays described herein can be used in the first 2 months post-transplant where commercial tests have not demonstrated utility. For example, in some embodiments, assays using the biomarkers described herein achieve a PPV of 5% and a NPV of 98-100% for samples obtained during the first 2 months after the heart transplant.

In a fourth aspect, a kit for determination of the acute rejection status of heart transplant in a patient is provided. The kit comprises a plurality of detection reagents that detect the nucleic acid expression of two or more nucleic acid markers in Table 3 or two or more proteomic markers in Table 4, or a combination of nucleic acid markers and proteomic markers selected from Table 3 and Table 4, respectively.

DETAILED DESCRIPTION OF THE INVENTION

Figure 1:
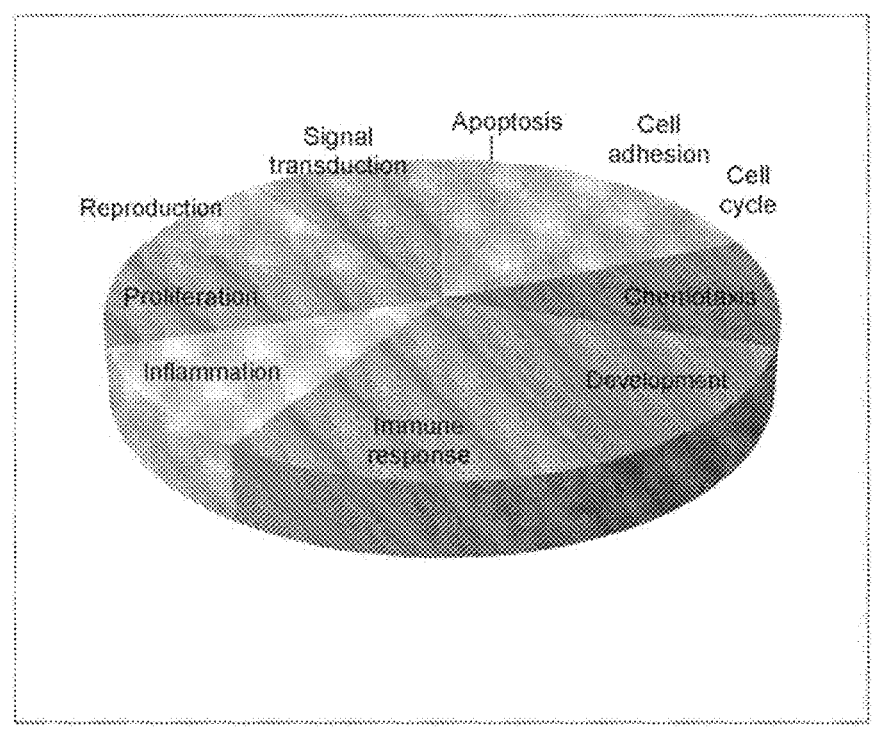
FIG. 1 shows a range of biological processes in which the nucleic acid markers disclosed herein participate.

In the description that follows, a number of terms are used extensively, the following definitions are provided to facilitate understanding of various aspects of the invention. Use of examples in the specification, including examples of terms, is for illustrative purposes only and is not intended to limit the scope and meaning of the embodiments of the invention herein. Numeric ranges are inclusive of the numbers defining the range. In the specification, the word "comprising" is used as an open-ended term, substantially equivalent to the phrase "including, but not limited to," and the word "comprises" has a corresponding meaning.

The present disclosure provides methods for diagnosing rejection in a subject that has received a tissue or organ allograft, specifically a cardiac allograft such as a heart transplant.

The present disclosure provides nucleic acid and proteomic expression profiles related to the assessment, prediction or diagnosis of allograft rejection in a subject. The specific combination of the altered expression levels (increased or decreased relative to a control) of specific sets of genomic or proteomic markers comprise a novel combination useful for assessment, prediction or diagnosis of allograft rejection in a subject.

An allograft is an organ or tissue transplanted between two genetically different subjects of the same species. The subject receiving the allograft is the 'recipient', while the subject providing the allograft is the 'donor'. A tissue or organ allograft may alternately be referred to as a 'transplant', a 'graft', an 'allograft', a 'donor tissue' or 'donor organ', or similar terms. A transplant between two subjects of different species is a xenograft.

Subjects may present with a variety of symptoms or clinical variables well-known in the literature, however none of these of itself is a predictive or diagnostic of allograft rejection. A myriad of clinical variables may be used in assessing a subject having, or suspected of having, allograft rejection, in addition to biopsy of the allograft. The information gleaned from these clinical variables is then used by a clinician, physician, veterinarian or other practitioner in a clinical field in attempts to determine if rejection is occurring, and how rapidly it progresses, to allow for modification of the immunosuppressive drug therapy of the subject. Examples of clinical variables are described in Table 2.

TABLE 2

Clinical variables for possible use in assessment of allograft rejection.

| Clinical Variable Name | Renal/Heart/ Liver/All | Variable Explanation |
| --- | --- | --- |
| Primary Diagnosis | All | Diagnosis leading to transplant |
| Secondary Diagnosis | All | Diagnosis leading to transplant |
| "Transplant Procedure - Living related, Living unrelated, or cadaveric" | | |
| Blood Type | All | Blood Type |
| Blood Rh | All | Blood Rh |
| Height (cm) | All | Height (cm) |
| Weight (kg) | All | Weight (kg) |
| BMI | All | Calculation: Weight/ (Height)2 |
| Liver Ascites | All | |
| HLA A1 | All | |
| HLA A2 | All | |
| HLA B1 | All | |
| HLA B2 | All | |
| HLA DR1 | All | |
| HLA DR2 | All | |
| CMV | All | Viral Status |
| CMV Date | All | Date of viral status |
| HIV | All | Viral Status |
| HBV | All | Viral Status |
| HBV Date | All | Date of viral status |
| HbsAb | All | Viral Status |
| HbcAb (Total) | All | Viral Status |
| HBvDNA | All | Viral Status |
| HCV | All | Viral Status |
| HCV Genotype | All | Hepatitis C genotype |
| HCV Genotype Sub | All | "Hepatitis C genotype, subtype" |
| EBV | All | Viral Status |
| Zoster | All | Viral Status |
| Dialysis Start Date | All | Dialysis Start Date |
| Dialysis Type | All | Dialysis Type |
| Cytoxicity Current Level | All | |
| Cytoxicity Current Date | All | |

TABLE 2-continued

Clinical variables for possible use in assessment of allograft rejection.

| Clinical Variable Name | Renal/Heart/Liver/All | Variable Explanation |
|---|---|---|
| Cytoxicity Peak Level | All | |
| Cytoxicity Peak Date | All | |
| Flush Soln | All | Type of Flush Solution used at transplant |
| Cold Time 1 | All | |
| Cold Time 2 | All | |
| Re-Warm Time 1 | All | |
| Re-Warm Time 2 | All | |
| HTLV 1 | All | |
| HTLV 2 | All | |
| HCV RNA | All | |
| 24 hr Urine | All | 24 Hour urine output |
| Systolic Blood Pressure | All | Blood Pressure reading |
| Diastolic Blood Pressure | All | Blood Pressure reading |
| 24 Hr Urine | All | 24 hour urine |
| Sodium | All | Blood test |
| Potassium | All | Blood test |
| Chloride | All | Blood test |
| Total CO2 | All | Blood test |
| Albumin | All | Blood test |
| Protein | All | Blood test |
| Calcium | All | Blood test |
| Inorganic Phosphate | All | Blood test |
| Magnesium | All | Blood test |
| Uric Acid | All | Blood test |
| Glucose | All | Blood test |
| Hemoglobin A1C | All | Blood test |
| CPK | All | Blood test |
| Parathyroid Hormone | All | Blood test |
| Homocysteine | All | Blood test |
| Urine Protein | All | Urine test |
| Creatinine | All | Blood test |
| BUN | All | Blood test |
| Hemaglobin | All | Blood test |
| Platelet Count | All | Blood test |
| WBC Count | All | Blood test |
| Prothrombin Time | All | Blood test |
| Partial Thromboplastin Time | All | Blood test |
| INR | All | Blood test |
| Gamma GT | All | Blood test |
| AST | All | Blood test |
| Alkaline Phosphatase | All | Blood test |
| Amylase | All | Blood test |
| Total Bilirubin | All | Blood test |
| Direct Bilirubin | All | Blood test |
| LDH | All | Blood test |
| ALT | All | Blood test |
| Triglycerides | All | Blood test |
| Cholesterol | All | Blood test |
| HDL Cholesterol | All | Blood test |
| LDL Cholesterol | All | Blood test |
| FEV1 | All | Lung function test |
| FVC | All | Lung function test |
| Total Ferritin | All | Blood test |
| TIBC | All | Blood test |
| Transferrin Saturated | All | Blood test |
| Ferritin | All | Blood test |
| Angiography | Heart | Heart function test |
| Intravascular ultrasound | Heart | Heart function test |
| Dobutamine Stress Echocardiography | Heart | Heart function test |
| Cyclosporine WB | All | Immunosuppressive levels |
| Cyclosporine 2 hr | All | Immunosuppressive levels |
| Tacrolimus WB | All | Immunosuppressive levels |
| Sirolimus WB | All | Immunosuppressive total daily dose |
| Solumedrol | All | Immunosuppressive total daily dose |
| Prednisone | All | Immunosuppressive total daily dose |
| Prednisone ALT | All | Immunosuppressive total daily dose |
| Tacrolimus | All | Immunosuppressive total daily dose |
| Cyclosporine | All | Immunosuppressive total daily dose |
| Imuran | All | Immunosuppressive total daily dose |
| Mycophonelate Mofetil | All | Immunosuppressive total daily dose |
| Sirolimus | All | Immunosuppressive total daily dose |
| OKT3 | All | Immunosuppressive total daily dose |
| ATG | All | Immunosuppressive total daily dose |
| ALG | All | Immunosuppressive total daily dose |
| Basiliximab | All | Immunosuppressive total daily dose |
| Daclizumab | All | Immunosuppressive total daily dose |
| Ganciclovir | All | Anti-viral total daily dose |
| Lamivudine | All | Anti-viral total daily dose |
| Riboviron | All | Anti-viral total daily dose |
| Interferon | All | Anti-viral total daily dose |
| Hepatisis C Virus RNA | All | test for presence of HCV values ( ) |
| CMV Antigenemia | All | Antiviral and Virus |
| Valganciclovir | All | Anti-viral total daily dose |
| Neutrophil Number | All | Blood test |
| C Peptide | All | Blood test |
| Peg Interferon | All | Anti-viral total daily dose |
| GFR | All | Glomerular Filtration Rate |
| Complication Events | All | Complication Type |
| Biopsy Scores | Renal | Borderline, 1A, 1B, 2A, 2B, 3, Hyperacute |
| Biopsy Scores | Liver | Portal inflammation, Bile duct inflammation damage, Venous endothelial inflammation each scored from 1 to 3 |
| Donor Blood Type | All | Donor Blood Type |
| Donor Blood Rh | All | Donor Rh |
| Donor HLA A1 | All | Donor HLA A1 |
| Donor HLA A2 | All | Donor HLA A2 |
| Donor HLA B1 | All | Donor HLA B1 |
| Donor HLA B2 | All | Donor HLA B2 |
| Donor HLA DR1 | All | Donor HLA DR1 |
| Donor HLA DR2 | All | Donor HLA DR2 |
| Donor CMV | All | Donor CMV |
| Donor HIV | All | Donor HIV |
| Donor HBV | All | Donor HBV |
| Donor HbsAb | All | Donor HbsAb |
| Donor HbcAb (total) | All | Donor HbcAb (total) |
| Donor Hbdna | All | Donor Hbdna |
| Donor HCV | All | Donor HCV |
| Donor EBV | All | Donor EBV |

Clinical variables (optionally accompanied by biopsy), while currently the only practical tools available to a clinician in mainstream medical practice, are not always able to cleanly differentiate between an AR (an "acute rejector"; ISHLT grade 2 R or higher) and an NR (a "mild or non-rejector"; ISHLT grade 0R or 1R) subject. While the extreme left and right subjects are correctly classified as AR or NR, the bulk of the subjects are represented in the middle range and their status is unclear. This does not negate the value of the clinical variables in the assessment of allograft rejection, but instead indicates their limitation when used in the absence of other methods.

The multifactorial nature of allograft rejection prediction, diagnosis and assessment is considered in the art to exclude the possibility of a single biomarker that meets even one of the needs of prediction, diagnosis or assessment of allograft rejection. Strategies involving a plurality of markers may take into account this multifactorial nature. Alternately, a plurality of markers may be assessed in combination with clinical variables that are less invasive (e.g. a biopsy not required) to tailor the prediction, diagnosis and/or assessment of allograft rejection in a subject.

Regardless of the methods used for prediction, diagnosis and assessment of allograft rejection, earlier is better—from the viewpoint of preserving organ or tissue function and preventing more systemic detrimental effects. There is no 'cure' for allograft rejection, only maintenance of the subject at a suitably immunosuppressed state, or in some cases, replacement of the organ if rejection has progressed too rapidly or is too severe to correct with immunosuppressive drug intervention therapy.

Applying a plurality of mathematical and/or statistical analytical methods to a protein or polypeptide dataset or nucleic acid expression dataset may indicate varying subsets of significant markers, leading to uncertainty as to which method is 'best' or 'more accurate'. Regardless of the mathematics, the underlying biology is the same in a dataset. By applying a plurality of mathematical and/or statistical methods to a microarray dataset and assessing the statistically significant subsets of each for common markers, uncertainty may be reduced, and clinically relevant core group of markers may be identified.

"Markers", "biological markers" or "biomarkers" may be used interchangeably and refer generally to detectable (and in some cases quantifiable) molecules or compounds in a biological sample. A marker may be down-regulated (decreased), up-regulated (increased) or effectively unchanged in a subject following transplantation of an allograft. Markers may include nucleic acids (DNA or RNA), a gene, or a transcript, or a portion or fragment of a transcript in reference to 'genomic' markers (alternately referred to as "nucleic acid markers"); polypeptides, peptides, proteins, isoforms, or fragments or portions thereof for 'proteomic' markers, or selected molecules, their precursors, intermediates or breakdown products (e.g. fatty acid, amino acid, sugars, hormones, or fragments or subunits thereof). In some usages, these terms may reference the level or quantity of a particular protein, peptide, nucleic acid or polynucleotide (in absolute terms or relative to another sample or standard value) or the ratio between the levels of two proteins, polynucleotides, peptides in a subject's biological sample. The level may be expressed as a concentration, for example micrograms per milliliter; as a colorimetric intensity, for example 0.0 being transparent and 1.0 being opaque at a particular wavelength of light, with the experimental sample ranked accordingly and receiving a numerical score based on transmission or absorption of light at a particular wavelength; or as relevant for other means for quantifying a marker, such as are known in the art. hi some examples, a ratio may be expressed as a unitless value. A "marker" may also reference to a ratio, or a net value following subtraction of a baseline value. A marker may also be represented as a 'fold-change', with or without an indicator of directionality (increase or decrease/up or down). The increase or decrease in expression of a marker may also be referred to as 'down-regulation' or 'up-regulation', or similar indicators of an increase or decrease in response to a stimulus, physiological event, or condition of the subject. A marker may be present in a first biological sample, and absent in a second biological sample; alternately the marker may be present in both, with a statistically significant difference between the two. Expression of the presence, absence or relative levels of a marker in a biological sample may be dependent on the nature of the assay used to quantify or assess the marker, and the manner of such expression will be familiar to those skilled in the art.

A marker may be described as being differentially expressed when the level of expression in a subject who is rejecting an allograft is significantly different from that of a subject or sample taken from a non-rejecting subject. A differentially expressed marker may be overexpressed or underexpressed as compared to the expression level of a normal or control sample.

A "profile" is a set of one or more markers and their presence, absence, relative level or abundance (relative to one or more controls). For example, a proteomic profile is a dataset of the presence, absence, relative level or abundance of proteomic markers. A genomic or nucleic acid profile a dataset of the presence, absence, relative level or abundance of expressed nucleic acids (e.g. transcripts, mRNA, EST or the like). A profile may alternately be referred to as an expression profile.

The increase or decrease, or quantification of the markers in the biological sample may be determined by any of several methods known in the art for measuring the presence and/or relative abundance of a gene product or transcript, or a nucleic acid molecule comprising a particular sequence, polypeptide or protein or the like. The level of the markers may be determined as an absolute value, or relative to a baseline value, and the level of the subject's markers compared to a cutoff index (e.g. a non-rejection cutoff index). Alternately the relative abundance of the marker may be determined relative to a control. The control may be a clinically normal subject (e.g. one who has not received an allograft) or may be an allograft recipient that has not previously demonstrated rejection.

In some embodiments, the control may be an autologous control, for example a sample or profile obtained from the subject before undergoing allograft transplantation. In some embodiments, the profile obtained at one time point (before, after or before and after transplantation) may be compared to one or more than one profiles obtained previously from the same subject. By repeatedly sampling the same biological sample from the same subject over time, a composite profile, illustrating marker level or expression over time may be provided. Sequential samples can also be obtained from the subject and a profile obtained for each, to allow the course of increase or decrease in one or more markers to be followed over time For example, an initial sample or samples may be taken before the transplantation, with subsequent samples being taken weekly, biweekly, monthly, bimonthly or at another suitable, regular interval and compared with profiles from samples taken previously. Samples may also be taken before, during and after administration of a course of a drug, for example an immunosuppressive drug.

Techniques, methods, tools, algorithms, reagents and other necessary aspects of assays that may be employed to detect and/or quantify a particular marker or set of markers are varied. Of significance is not so much the particular method used to detect the marker or set of markers, but what markers to detect. As is reflected in the literature, tremendous variation is possible. Once the marker or set of markers to be detected or quantified is identified, any of several techniques may be well suited, with the provision of appropriate reagents. One of skill in the art, when provided with the set of markers to be identified, will be capable of selecting the appropriate assay (for example, a PCR based or a microarray based assay for nucleic acid markers, an ELISA, protein or antibody microarray or similar immunologic assay, or in some examples, use of an MRM, iTRAQ, iCAT or SELDI proteomic mass spectrometric based method) for performing the methods disclosed herein.

The present disclosure provides nucleic acid expression profiles and proteomic expression profiles related to the assessment, prediction or diagnosis of allograft rejection in a subject.

For example, detection or determination, and in some cases quantification, of a nucleic acid may be accomplished by any one of a number methods or assays employing recombinant DNA technologies known in the art, including but not limited to, as sequence-specific hybridization, polymerase chain reaction (PCR), RT-PCR, microarrays and the like. Such assays may include sequence-specific hybridization, primer extension, or invasive cleavage. Furthermore, there are numerous methods for analyzing/detecting the products of each type of reaction (for example, fluorescence, luminescence, mass measurement, electrophoresis, etc.). Furthermore, reactions can occur in solution or on a solid support such as a glass slide, a chip, a bead, or the like.

Methods of designing and selecting probes for use in microarrays or biochips, or for selecting or designing primers for use in PCR-based assays are known in the art. Once the marker or markers are identified and the sequence of the nucleic acid determined by, for example, querying a database comprising such sequences, or by having an appropriate sequence provided (for example, a sequence listing as provided herein), one of skill in the art will be able to use such information to select appropriate probes or primers and perform the selected assay.

Standard reference works setting forth the general principles of recombinant DNA technologies known to those of skill in the art include, for example: Ausubel et al, Current Protocols In Molecular Biology, John Wiley and Sons, New York (1998 and Supplements to 2001); Sambrook et al, Molecular Cloning: A Laboratory Manual, 2d Ed., Cold Spring Harbor Laboratory Press, Plainview, N.Y. (1989); Kaufman et al, Eds., Handbook Of Molecular And Cellular Methods In Biology And Medicine, CRC Press, Boca Raton (1995); McPherson, Ed., Directed Mutagenesis: A Practical Approach, IRL Press, Oxford (1991).

Proteins, protein complexes or proteomic markers may be specifically identified and/or quantified by a variety of methods known in the art and may be used alone or in combination. Immunologic- or antibody-based techniques include enzyme-linked immunosorbent assay (ELISA), radioimmunoassay (RIA), western blotting, immunofluorescence, microarrays, some chromatographic techniques (i.e. immunoaffinity chromatography), flow cytometry, immunoprecipitation and the like. Such methods are based on the specificity of an antibody or antibodies for a particular epitope or combination of epitopes associated with the protein or protein complex of interest. Non-immunologic methods include those based on physical characteristics of the protein or protein complex itself. Examples of such methods include electrophoresis, some chromatographic techniques (e.g. high performance liquid chromatography (HPLC), fast protein liquid chromatography (FPLC), affinity chromatography, ion exchange chromatography, size exclusion chromatography and the like), mass spectrometry, sequencing, protease digests, and the like. Such methods are based on the mass, charge, hydrophobicity or hydrophilicity, which is derived from the amino acid complement of the protein or protein complex, and the specific sequence of the amino acids. Examples of methods employing mass spectrometry include those described in, for example, PCT Publication WO 2004/019000, WO 2000/00208, U.S. Pat. No. 6,670,194. Immunologic and non-immunologic methods may be combined to identify or characterize a protein or protein complex. Furthermore, there are numerous methods for analyzing/detecting the products of each type of reaction (for example, fluorescence, luminescence, mass measurement, electrophoresis, etc.). Furthermore, reactions can occur in solution or on a solid support such as a glass slide, a chip, a bead, or the like.

Methods of producing antibodies for use in protein or antibody arrays, or other immunology based assays are known in the art. Once the marker or markers are identified and the amino acid sequence of the protein or polypeptide is identified, either by querying of a database or by having an appropriate sequence provided (for example, a sequence listing as provide herein), one of skill in the art will be able to use such information to prepare one or more appropriate antibodies and perform the selected assay.

For preparation of monoclonal antibodies directed towards a biomarker, any technique that provides for the production of antibody molecules by continuous cell lines in culture may be used. Such techniques include, but are not limited to, the hybridoma technique originally developed by Kohler and Milstein (1975, Nature 256:495-497), the trioma technique (Gustafsson et al., 1991, Hum. Antibodies Hybridomas 2:26-32), the human B-cell hybridoma technique (Kozbor et al., 1983, Immunology Today 4:72), and the EBV hybridoma technique to produce human monoclonal antibodies (Cole et al., 1985, In: Monoclonal Antibodies and Cancer Therapy, Alan R. Liss, Inc., pp. 77-96). Human antibodies may be used and can be obtained by using human hybridomas (Cote et al., 1983, Proc. Natl. Acad. Sci. USA 80:2026-2030) or by transforming human B cells with EBV virus in vitro (Cole et al., 1985, In: Monoclonal Antibodies and Cancer Therapy, Alan R. Liss, Inc., pp. 77-96). Techniques developed for the production of "chimeric antibodies" (Morrison et al, 1984, Proc. Natl. Acad. Sci. USA 81:6851-6855; Neuberger et al, 1984, Nature 312:604-608; Takeda et al, 1985, Nature 314:452-454) by splicing the genes from a mouse antibody molecule specific for a biomarker together with genes from a human antibody molecule of appropriate biological activity can be used; such antibodies are within the scope of this invention. Techniques described for the production of single chain antibodies (U.S. Pat. No. 4,946,778) can be adapted to produce a biomarker-specific antibodies. An additional embodiment of the invention utilizes the techniques described for) the construction of Fab expression libraries (Huse et al, 1989, Science 246: 1275-1281) to allow rapid and easy identification of monoclonal Fab fragments with the desired specificity for a biomarker proteins. Non-human antibodies can be "humanized" by known methods (e.g., U.S. Pat. No. 5,225,539).

Antibody fragments that contain the idiotypes of a biomarker can be generated by techniques known in the art. For example, such fragments include, but are not limited to, the F(ab')2 fragment which can be produced by pepsin digestion of the antibody molecule; the Fab' fragment that can be generated by reducing the disulfide bridges of the F(ab')2 fragment; the Fab fragment that can be generated by treating the antibody molecular with papain and a reducing agent; and Fv fragments. Synthetic antibodies, e.g., antibodies produced by chemical synthesis, are useful in the present invention.

Standard reference works described herein and known to those skilled in the relevant art describe both immunologic and non-immunologic techniques, their suitability for particular sample types, antibodies, proteins or analyses. Standard reference works setting forth the general principles of immunology and assays employing immunologic methods known to those of skill in the art include, for example: Harlow and Lane, Antibodies: A Laboratory Manual, 2d Ed., Cold Spring Harbor Laboratory Press, Cold Spring Harbor, N.Y. (1999); Harlow and Lane, Using Antibodies: A Laboratory Manual. Cold Spring Harbor Laboratory Press, New York; Coligan et al. eds. Current Protocols in Immunology, John Wiley and Sons, New York, N.Y. (1992-2006); and Roitt et al., Immunology, 3d Ed., Mosby-Year Book Europe Limited, London (1993).

Standard reference works setting forth the general principles of peptide synthesis technology and methods known to those of skill in the art include, for example: Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley and Sons, N Y, 1994).

A subject's rejection status may be described as an "acute rejector" (ISHLT grade 2R of higher; AR) or as a "non-rejector" (ISHLT grade 0R or 1R; NR) and is determined by comparison of the concentration of the markers to that of a non-rejector cutoff index. A "non-rejector cutoff index" is a numerical value or score, beyond or outside of which a subject is categorized as having an AR rejection status. The non-rejector cutoff index maybe alternately referred to as a 'control value', a 'control index', or simply as a 'control'. A non-rejector cutoff-index maybe the concentration of individual markers in a control subject population and considered separately for each marker measured; alternately the non-rejector cutoff index may be a combination of the concentration of the markers, and compared to a combination of the concentration of the markers in the subject's sample provided for diagnosing. The control subject population may be a normal or healthy control population, or may be an allograft recipient population that has not, or is not, rejecting the allograft. The control maybe a single subject, and for some embodiments, maybe an autologous control. A control, or pool of controls, may be constant e.g. represented by a static value, or may be cumulative, in that the sample population used to obtain it may change from site to site, or over time and incorporate additional data points. For example, a central data repository, such as a centralized healthcare information system, may receive and store data obtained at various sites (hospitals, clinical laboratories or the like) and provide this cumulative data set for use with the methods of the invention at a single hospital, community clinic, for access by an end user (i.e. an individual medical practitioner, medical clinic or center, or the like).

The non-rejector cutoff index may be alternately referred to as a 'control value', a 'control index' or simply as a 'control'. In some embodiments the cutoff index may be further characterized as being a genomic cutoff index (for genomic expression profiling of subjects), a proteomic cutoff index (for proteomic profiling of subjects), or the like.

A "biological sample" refers generally to body fluid or tissue or organ sample from a subject. For example, the biological sample may a body fluid such as blood, plasma, lymph fluid, serum, urine or saliva. A tissue or organ sample, such as a non-liquid tissue sample maybe digested, extracted or otherwise rendered to a liquid form—examples of such tissues or organs include cultured cells, blood cells, skin, liver, heart, kidney, pancreas, islets of Langerhans, bone marrow, blood, blood vessels, heart valve, lung, intestine, bowel, spleen, bladder, penis, face, hand, bone, muscle, fat, cornea or the like. A plurality of biological samples may be collected at any one time. A biological sample or samples may be taken from a subject at any time, including before allograft transplantation, at the time of translation or at anytime following transplantation. A biological sample may comprise nucleic acid, such as deoxyribonucleic acid or ribonucleic acid, or a combination thereof, in either single or double-stranded form. When an organ is removed from a donor, the spleen of the donor or a part of it may be kept as a biological sample from which to obtain donor T-cells. When an organ is removed from a living donor, a blood sample may be taken, from which donor T-cells may be obtained. Alloreactive T-cells may be isolated by exploiting their specific interaction with antigens (including the MHC complexes) of the allograft. Methods to enable specific isolation of alloreactive T-cells are described in, for example PCT Publication WO 2005/05721, herein incorporated by reference.

A lymphocyte is nucleated or 'white' blood cell (leukocyte) of lymphoid stem cell origin. Lymphocytes include T-cells, B-cells natural killer cells and the like, and other immune regulatory cells. A "T-cell" is a class of lymphocyte responsible for cell-mediated immunity, and for stimulating B-cells. A stimulated B-cell produces antibodies for specific antigens. Both B-cells and T-cells function to recognize non-self antigens in a subject. Non-self antigens include those of viruses, bacteria and other infectious agents as well as allografts.

The term "subject" or "patient" generally refers to mammals and other animals including humans and other primates, companion animals, zoo, and farm animals, including, but not limited to, cats, dogs, rodents, rats, mice, hamsters, rabbits, horses, cows, sheep, pigs, goats, poultry, etc. A subject includes one who is to be tested, or has been tested for prediction, assessment or diagnosis of allograft rejection. The subject may have been previously assessed or diagnosed using other methods, such as those described herein or those in current clinical practice, or maybe selected as part of a general population (a control subject).

A fold-change of a marker in a subject, relative to a control maybe at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 or more, or any amount therebetween. The fold change may represent a decrease, or an increase, compared to the control value.

One or more than one includes 1, 2, 3, 4, 5, 6, 7, 8, 9, 10, 11, 12, 13, 14, 15, 16 or more.

"Down-regulation" or 'down-regulated may be used interchangeably and refer to a decrease in the level of a marker, such as a gene, nucleic acid, transcript, protein or polypeptide. "Up-regulation" or "up-regulated" may be used interchangeably and refer to an increase in the level of a marker, such as a gene, nucleic acid, transcript, protein or polypeptide.

For the purpose of this invention, a patient has treatable acute rejection status to heart transplant if he or she had response that fits into the "2R" or "3R" category according to the International Society for heart and Lung transplantation standard (Table 1). A patient has non rejection status if the response to heart transplant fit into the "0R" category and moderate rejection status if the response fits into the "1R" category according to the above standard.

Once a subject is identified as an acute rejector, or at risk for becoming an acute rejector by any method (genomic, proteomic, or a combination thereof), therapeutic measures may be implemented to alter the subject's immune response to the allograft. The subject may undergo additional monitoring of clinical values more frequently, or using more sensitive monitoring methods. Additionally the subject may be administered immunosuppressive medicaments to decrease or increase the subject's immune response. Even though a subject's immune response needs to be suppressed to prevent rejection of the allograft, a suitable level of immune function is also needed to protect against opportunistic infection. Various medicaments that maybe administered to a subject are known; see for example, Goodman and Gilman's The Pharmacological Basis of Therapeutics 11th edition. Ch 52, pp 1405-1431 and references therein; L L Brunton, J S Lazo, K L Parker editors. Standard reference works setting forth the general principles of medical physiology and pharmacology known to those of skill in the art include: Fauci et al., Eds., Harrison's Principles Of Internal Medicine, 14th Ed., McGraw-Hill Companies, Inc. (1998). Other preventative and therapeutic strategies are reviewed in the medical literature—see, for example Kobashigawa et al. 2006. Nature Clinical Practice. Cardiovascular Medicine 3:203-21.

Genomic Nucleic Acid Expression Profiling

A method of diagnosing acute allograft rejection in a subject as provided by the present invention comprises 1) determining the expression profile of one or more than one nucleic acid markers in a biological sample from the subject, the nucleic acid markers selected from the group consisting of the nucleic acid markers listed in Table 3, 5, or 7; 2) comparing the expression profile of the one or more than one nucleic acid markers to a non-rejector profile; and 3) determining whether the expression level of the one or more than one nucleic acid markers is up-regulated or down-regulated relative to the control profile, wherein up-regulation or down-regulation of the one or more than one nucleic acid markers is indicative of the rejection status.

Therefore, the invention also provides for a method of predicting, assessing or diagnosing allograft rejection in a subject as provided by the present invention comprises 1) measuring the increase or decrease of one or more than one nucleic acid markers selected from the group consisting of the nucleic acid markers listed in Table 3, 5, or 7; and 2) determining the 'rejection status' of the subject, wherein the determination of 'rejection status' of the subject is based on comparison of the subject's nucleic acid marker expression profile to a control nucleic acid marker expression profile.

The phrase "gene expression data", "gene expression profile" "nucleic acid expression profile" or "marker expression profile" as used herein refers to information regarding the relative or absolute level of expression of a gene or set of genes in a biological sample. The level of expression of a gene may be determined based on the level of a nucleic acid such as RNA including mRNA, transcribed from or encoded by the gene.

A "polynucleotide", "oligonucleotide", "nucleic acid" or "nucleotide polymer" as used herein may include synthetic or mixed polymers of nucleic acids, including RNA, DNA or both RNA and DNA, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e. g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

An oligonucleotide includes variable length nucleic acids, which may be useful as probes, primers and in the manufacture of microarrays (arrays) for the detection and/or amplification of specific nucleic acids. Oligonucleotides may comprise DNA, RNA, PNA or other polynucleotide moieties as described in, for example, U.S. Pat. No. 5,948,902. Such DNA, RNA or oligonucleotide strands may be synthesized by the sequential addition (5 '-3' or 3'-5') of activated monomers to a growing chain which may be linked to an insoluble support. Numerous methods are known in the art for synthesizing oligonucleotides for subsequent individual use or as a part of the insoluble support, for example in arrays (BERNFIELD M R. and ROTTMAN F M. J. Biol. Chem. (1967) 242(18):4134-43; SULSTON J. et al. PNAS (1968) 60(2):409-415; GILLAM S. et al. Nucleic Acid Res. (1975) 2(5):613-624; BONORA G M. et al. Nucleic Acid Res. (1990) 18(11):3155-9; LASHKARI D A. et al. PNAS (1995) 92(17):7912-5; MCGALL G. et al. PNAS (1996) 93(24):13555-60; ALBERT T J. et al. Nucleic Acid Res. (2003) 31(7):e35; GAO X. et al. Biopolymers (2004) 73(5): 579-96; and MOORCROFT M J. et al. Nucleic Acid Res. (2005) 33(8):e75). In general, oligonucleotides are synthesized through the stepwise addition of activated and protected monomers under a variety of conditions depending on the method being used. Subsequently, specific protecting groups may be removed to allow for further elongation and subsequently and once synthesis is complete all the protecting groups may be removed and the oligonucleotides removed from their solid supports for purification of the complete chains if so desired.

A "gene" is an ordered sequence of nucleotides located in a particular position on a particular chromosome that encodes a specific functional product and may include untranslated and untranscribed sequences in proximity to the coding regions (5' and 3' to the coding sequence). Such non-coding sequences may contain regulatory sequences needed for transcription and translation of the sequence or splicing of introns, for example, or may as yet to have any function attributed to them beyond the occurrence of the mutation of interest. A gene may also include one or more promoters, enhancers, transcription factor binding sites, termination signals or other regulatory elements. A gene may be generally referred to as 'nucleic acid'.

The term "microarray," "array," or "chip" refers to a plurality of defined nucleic acid probes coupled to the surface of a substrate in defined locations. The substrate may be preferably solid. Microarrays, their methods of manufacture, use and analysis have been generally described in the art in, for example, U.S. Pat. No. 5,143,854 (Pirrung), U.S. Pat. No. 5,424,186 (Fodor), U.S. Pat. No. 5,445,934 (Fodor), U.S. Pat. No. 5,677,195 (Winkler), U.S. Pat. No. 5,744,305 (Fodor), U.S. Pat. No. 5,800,992 (Fodor), U.S. Pat. No. 6,040,193 (Winkler), and Fodor et al. 1991. Science, 251-0.161-111.

"Hybridization" includes a reaction in which one or more polynucleotides and/or oligonucleotides interact in an ordered manner (sequence-specific) to form a complex that is stabilized by hydrogen bonding—also referred to as 'Watson-Crick' base pairing. Variant base-pairing may also occur through non-canonical hydrogen bonding includes Hoogsteen base pairing. Under some thermodynamic, ionic or pH conditions, triple helices may occur, particularly with ribonucleic acids. These and other variant hydrogen bonding or base-pairing are known in the art, and may be found in, for example, Lehninger—Principles of Biochemistry, 3rd edition (Nelson and Cox, eds. Worth Publishers, New York.).

Hybridization reactions can be performed under conditions of different "stringency". The stringency of a hybridization reaction includes the difficulty with which any two nucleic acid molecules will hybridize to one another. Stringency may be increased, for example, by increasing the temperature at which hybridization occurs, by decreasing the ionic concentration at which hybridization occurs, or a combination thereof. Under stringent conditions, nucleic acid molecules at least 60 percent, 65 percent, 70 percent, 75 percent or more identical to each other remain hybridized to each other, whereas molecules with low percent identity cannot remain hybridized. An example of stringent hybridization conditions are hybridization in 6× sodium chloride/sodium citrate (SSC) at about 44-45 degrees centigrade, followed by one or more washes in 0.2×SSC, 0.1 percent SDS at 50 Degrees centigrade 55 Degrees centigrade 60 Degrees centigrade 65 degrees centigrade, or at a temperature therebetween.

Hybridization between two nucleic acids may occur in an antiparallel configuration—this is referred to as 'annealing', and the paired nucleic acids are described as complementary. A double-stranded polynucleotide may be "complementary", if hybridization can occur between one of the strands of the first polynucleotide and the second. The degree of which one polynucleotide is complementary with another is referred to as homology, and is quantifiable in terms of the proportion of bases in opposing strands that are expected to hydrogen bond with each other, according to generally accepted base-pairing rules.

In general, sequence-specific hybridization involves a hybridization probe, which is capable of specifically hybridizing to a defined sequence. Such probes may be designed to differentiate between sequences varying in only one or a few nucleotides, thus providing a high degree of specificity. A strategy which couples detection and sequence discrimination is the use of a "molecular beacon", whereby the hybridization probe (molecular beacon) has 3' and 5' reporter and quencher molecules and 3' and 5' sequences which are complementary such that absent an adequate binding target for the intervening sequence the probe will form a hairpin loop. The hairpin loop keeps the reporter and quencher in close proximity resulting in quenching of the fluorophor (reporter) which reduces fluorescence emissions. However, when the molecular beacon hybridizes to the target the fluorophor and the quencher are sufficiently separated to allow fluorescence to be emitted from the fluorophor.

Probes used in hybridization may include double-stranded DNA, single-stranded DNA and RNA oligonucleotides, and peptide nucleic acids. Hybridization conditions and methods for identifying markers that hybridize to a specific probe are described in the art—see, for example, Brown, T. "Hybridization Analysis of DNA Blots" in Current Protocols in Molecular Biology. F M Ausubel et al, editors. Wiley and Sons, 2003. doi: 10.1002/0471142727.mb0210s21. Suitable hybridization probes for use in accordance with the invention include oligonucleotides, polynucleotides or modified nucleic acids from about 10 to about 400 nucleotides, alternatively from about 20 to about 200 nucleotides, or from about 30 to about 100 nucleotides in length.

Specific sequences may be identified by hybridization with a primer or a probe, and this hybridization subsequently detected.

A "primer" includes a short polynucleotide, generally with a free 3'-OH group that binds to a target or "template" present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are well known in the art, and are taught, for example, in Beverly, S M. Enzymatic Amplification of RNA by PCR (RT-PCR) in Current Protocols in Molecular Biology. F M Ausubel et al, editors. Wiley and Sons, 2003. doi: 10.1002/0471142727.mb 1505s56. Synthesis of the replicate copies may include incorporation of a nucleotide having a label or tag, for example, a fluorescent molecule, biotin, or a radioactive molecule. The replicate copies may subsequently be detected via these tags, using conventional methods.

A primer may also be used as a probe in hybridization reactions, such as Southern or Northern blot analyses (see, e.g., Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

A "probe set" (or 'primer set') as used herein refers to a group of oligonucleotides that may be used to detect one or more expressed nucleic acids, or expressed genes. Detection may be, for example, through amplification as in PCR and RT-PCR, or through hybridization, as on a microarray, or through selective destruction and protection, as in assays based on the selective enzymatic degradation of single or double stranded nucleic acids. Probes in a probe set may be labeled with one or more fluorescent, radioactive or other detectable moieties (including enzymes). Probes may be any size so long as the probe is sufficiently large to selectively detect the desired gene—generally a size range from about 15 to about 25, or to about 30 nucleotides is of sufficient size. A probe set maybe in solution, e.g. for use in multiplex PCR. Alternately, a probe set may be adhered to a solid surface, as in an array or microarray.

In some embodiments of the invention, a probe set for detection of nucleic acids expressed by a set of genomic markers comprising one or more of nucleic acid markers in Table 3, 5, or 7. is provided. Such a probe set may be useful for determining the rejection status of a subject. The probe set may comprise one or more pairs of primers for specific amplification (e.g. PCR or RT-PCR) of nucleic acid sequences corresponding to one or more of the nucleic acid markers in Table 3, 5, or 7. In another embodiment of the invention, the probe set is part of a microarray.

It will be appreciated that numerous other methods for sequence discrimination and detection are known in the art and some of which are described in further detail below. It will also be appreciated that reactions such as arrayed primer extension mini sequencing, tag microarrays and sequence-specific extension could be performed on a microarray. One such array based genotyping platform is the microsphere based tag-it high throughput array (BORTOLINS. et al. 2004 Clinical Chemistry 50: 2028-36). This method amplifies genomic DNA by PCR followed by sequence-specific primer extension with universally tagged primers. The products are then sorted on a Tag-It array and detected using the Luminex xMAP system.

It will be appreciated by a person of skill in the art that any numerical designations of nucleotides or amino acids within a sequence are relative to the specific sequence. Also, the same positions may be assigned different numerical designations depending on the way in which the sequence is numbered and the sequence chosen. Furthermore, sequence variations such as insertions or deletions, may change the relative position and subsequently the numerical designations of particular nucleotides or amino acids at or around a mutational site.

Selection and/or design of probes, primers or probe sets for specific detection of expression of any gene of interest, including any of the above genes in Table 3, 5, or 7, is within the ability of one of skill in the relevant art, when provided with one or more nucleic acid sequences of the gene of interest. Further, any of several probes, primers or probe sets, or a plurality of probes, primers or probe sets may be used to detect a gene of interest, for example, an array may include multiple probes for a single gene transcript—the aspects of the invention as described herein are not limited to any specific probes exemplified.

Sequence identity or sequence similarity may be determined using a nucleotide sequence comparison program (for DNA or RNA sequences, or fragments or portions thereof) or an amino acid sequence comparison program (for protein, polypeptide or peptide sequences, or fragments or portions thereof), such as that provided within DNASIS (for example, but not limited to, using the following parameters: GAP penalty 5, #of top diagonals 5, fixed GAP penalty 10, k-tuple 2, floating gap 10, and window size 5). However, other methods of alignment of sequences for comparison are well-known in the art for example the algorithms of Smith and Waterman (1981, Adv. Appl. Math. 2:482), Needleman and Wunsch (J. MoI. Biol. 48:443, 1970), Pearson and Lipman (1988, Proc. Nat'l. Acad. Sci. USA 85:2444), and by computerized implementations of these algorithms (e.g. GAP, BESTFIT, FASTA, and BLAST), or by manual alignment and visual inspection.

If a nucleic acid or gene, polypeptide or sequence of interest is identified and a portion or fragment of the sequence (or sequence of the gene polypeptide or the like) is provided, other sequences that are similar, or substantially similar may be identified using the programs exemplified above. For example, when constructing a microarray or probe sequences, the sequence and location are known, such that if a microarray experiment identifies a 'hit' (the probe at a particular location hybridizes with one or more nucleic acids in a sample, the sequence of the probe will be known (either by the manufacturer or producer of the microarray, or from a database provided by the manufacturer—for example the NetAffx databases of Affymetrix, the manufacturer of the Human Genome U133 Plus 2.0 Array). If the identity of the sequence source is not provided, it may be determined by using the sequence of the probe in a sequence-based search of one or more databases. For peptide or peptide fragments identified by proteomics assays, for example iTRAQ, the sequence of the peptide or fragment may be used to query databases of amino acid sequences as described above. Examples of such a database include those maintained by the National Centre for Biotechnology Information, or those maintained by the European Bioinformatics Institute.

A protein or polypeptide, nucleic acid or fragment or portion thereof may be considered to be specifically identified when its sequence may be differentiated from others found in the same phylogenetic Species, Genus, Family or Order. Such differentiation may be identified by comparison of sequences. Comparisons of a sequence or sequences may be done using a BLAST algorithm (Altschul et al. 1009. J. MoI Biol 215:403-410). A BLAST search allows for comparison of a query sequence with a specific sequence or group of sequences, or with a larger library or database (e.g. GenBank or GenPept) of sequences, and identify not only sequences that exhibit 100 percent identity, but also those with lesser degrees of identity. For example, regarding a protein with multiple isoforms (either resulting from, for example, separate genes or variant splicing of the nucleic acid transcript from the gene, or post translational processing), an isoform may be specifically identified when it is differentiated from other isoforms from the same or a different species, by specific detection of a structure, sequence or motif that is present on one isoform and is absent, or not detectable on one or more other isoforms.

Access to the methods of the invention may be provided to an end user by, for example, a clinical laboratory or other testing facility performing the individual marker tests—the biological samples are provided to the facility where the individual tests and analyses are performed and the predictive method applied; alternately, a medical practitioner may receive the marker values from a clinical laboratory and use a local implementation or an internet-based implementation to access the predictive methods of the invention.

Determination of statistical parameters such as multiples of the median, standard error, standard deviation and the like, as well as other statistical analyses as described herein are known and within the skill of one versed in the relevant art. Use of a particular coefficient, value or index is exemplary only and is not intended to constrain the limits of the various aspects of the invention as disclosed herein.

Interpretation of the large body of gene expression data obtained from, for example, microarray experiments, or complex RT-PCR experiments may be a formidable task, but is greatly facilitated through use of algorithms and statistical tools designed to organize the data in a way that highlights systematic features. Visualization tools are also of value to represent differential expression by, for example, varying intensity and hue of colour (Eisen et al. 1998. Proc Natl Acad Sci 95:14863-14868). The algorithm and statistical tools available have increased in sophistication with the increase in complexity of arrays and the resulting datasets, and with the increase in processing speed, computer memory, and the relative decrease in cost of these.

Mathematical and statistical analysis of nucleic acid or protein expression profiles may accomplish several things—identification of groups of genes that demonstrate coordinate regulation in a pathway or a domain of a biological system, identification of similarities and differences between two or more biological samples, identification of features of a gene expression profile that differentiate between specific events or processes in a subject, or the like. This may include assessing the efficacy of a therapeutic regimen or a change in a therapeutic regimen, monitoring or detecting the development of a particular pathology, differentiating between two otherwise clinically similar (or almost identical) pathologies, or the like.

Clustering methods are known and have been applied to microarray datasets, for example, hierarchical clustering, self-organizing maps, k-means or deterministic annealing. (Eisen et al, 1998 Proc Natl Acad Sci USA 95:14863-14868; Tamayo, P., et al. 1999. Proc Natl Acad Sci USA 96:2907-2912; Tavazoie, S., et al. 1999. Nat Genet 22:281-285; Alon, U., et al. 1999. Proc Natl Acad Sci USA 96:6745-6750).

Such methods may be useful to identify groups of genes in a gene expression profile that demonstrate coordinate regulation, and also useful for the identification of novel genes of otherwise unknown function that are likely to participate in the same pathway or system as the others demonstrating coordinate regulation.

The pattern of nucleic acid or protein expression in a biological sample may also provide a distinctive and accessible molecular picture of its functional state and identity (DeRisi 1997; Cho 1998; Chu 1998; Holstege 1998; Spellman 1998). Two different samples that have related gene expression patterns are therefore likely to be biologically and functionally similar to one another, conversely two samples that demonstrate significant differences may not only be differentiated by the complex expression pattern displayed, but may indicate a diagnostic subset of gene products or transcripts that are indicative of a specific pathological state or other physiological condition, such as allograft rejection.

Genomic Expression Profiling Markers ("Genomic Markers")

The present invention provides for a core group of markers useful for the assessment, prediction or diagnosis of allograft rejection, including acute allograft rejection, comprising the nucleic acid markers in Table 3, 5, or 7.

The sensitivity of the assay to determine the acute rejection status of a heart transplant in a subject using panels of nucleic acid markers described herein may be at least 80%, at least 85%, at least 90%, at least 91%, at least 92%, at least 93%, at least 94%, at least 95%, at least 96%, at least 97%, at least 98%, at least 99%, or 100%. The specificity of the assay using the panels of nucleic acid markers may be at least 10%, at least 15%, at least 22%, at least 30%, at least 40%, at least 50%, at least 60%, at least 70%, at least 74%, at least 80%, at least 90%, at least 91%, or at least 95%. The PPV of the assay using the panels of the nucleic acid markers of the invention may be at least 2%, at least 4%, at least 5%, at least 7%, at least 14%, or at least 32%. The NPV of the assay using the panels of the proteomic markers may be at least 95%, at least 96%, at least 97%, at least 98%, at least 99%, or 100%.

The invention also provides for a kit for use in predicting or diagnosing a subject's rejection status. The kit may comprise reagents for specific and quantitative detection of one or more nucleic acid markers in Table 3, 5, or 7, along with instructions for the use of such reagents and methods for analyzing the resulting data. The kit may be used alone for predicting or diagnosing a subject's rejection status, or it may be used in conjunction with other methods for determining clinical variables, or other assays that may be deemed appropriate. The kit may include, for example, one or more labelled oligonucleotides capable of selectively hybridizing to the marker. The kit may further include, for example, one or more oligonucleotides operable to amplify a region of the marker (e.g. by PCR). Instructions or other information useful to combine the kit results with those of other assays to provide a non-rejection cutoff index for the prediction or diagnosis of a subject's rejection status may also be provided.

Proteomic Profiling for Diagnosing Allograft Rejection

Proteomic profiling may also be used for diagnosing allograft rejection. Proteomic profiling may be used alone, or in combination with genomic expression profiling.

In some embodiments, the invention provides for a method of diagnosing acute allograft rejection in a subject comprising 1) determining the expression profile of one or more than one proteomic markers in a biological sample from the subject, the proteomic markers selected from the group consisting of the polypeptides in Table 4; 2) comparing the expression profile of the one or more than one proteomic markers to a non-rejector profile; and 3) determining whether the expression level of the one or more than one proteomic markers is increased or decreased relative to the control profile, wherein increase or decrease of the one or more than one proteomic markers is indicative of the acute rejection status.

The invention also provides for a method of predicting, assessing or diagnosing allograft rejection in a subject as provided by the present invention comprises 1) measuring the increase or decrease of five or more than five proteomic markers selected from the group consisting of polypeptides in Table 4, and 2) determining the 'rejection status' of the subject, wherein the determination of 'rejection status' of the subject is based on comparison of the subject's proteomic marker expression profile to a control proteomic marker expression profile.

A myriad of non-labelling methods for protein identification and quantitation are currently available, such as glycopeptide capture (Zhang et al., 2005. Mol Cell Proteomics 4:144-155), multidimensional protein identification technology (Mud-PIT) Washburn et al., 2001 Nature Biotechnology (19:242-247), and surface-enhanced laser desorption ionization (SELDI-TOF) (Hutches et al., 1993. Rapid Commun Mass Spec 7:576-580). In addition, several isotope labelling methods which allow quantification of multiple protein samples, such as isobaric tags for relative and absolute protein quantification (iTRAQ) (Ross et al, 2004 Mol Cell Proteomics 3:1154-1169); isotope coded affinity tags (ICAT) (Gygi et al., 1999 Nature Biotechnology 17:994-999), isotope coded protein labelling (ICPL) (Schmidt et al., 2004. Proteomics 5:4-15), and N-terminal isotope tagging (NIT) (Fedjaev et al., 2007 Rapid Commun Mass Spectrom 21:2671-2679; Nam et al., 2005. J Chromatogr B Analyt Technol Biomed Life ScL 826:91-107), have become increasingly popular due to their high-throughput performance, a trait particular useful in biomarker screening/identification studies.

A multiplexed iTRAQ methodology was employed for identification of plasma proteomic markers in allograft recipients. iTRAQ was first described by Ross et al, 2004 (Mol Cell Proteomics 3:1154-1169). Briefly, subject plasma samples (control and allograft recipient) were depleted of the 14 most abundant proteins and quantitatively analyzed by iTRAQ-MALDI-TOF/TOF. resulted in the identification of about 200 medium-to-low abundant proteins per iTRAQ run and 1000 proteins cumulatively. Proteins that were detected in at least ⅔ of samples within AR and NR groups were considered for statistical analyses. Candidate plasma proteins with differential relative concentrations between AR and NR were identified. Two classifiers were constructed using LDA, a multivariate analysis that seeks for the linear combination of markers that best discriminates both groups. Results were validated further using additional samples (test set) from an extended cohort of patients. (A technical validation using ELISA was also performed and corroborated the results from iTRAQ. The ELISA results on their own demonstrated differential protein levels in AR versus NR samples.

Thus, although single candidate biomarkers may not clearly differentiate groups (with some fold-changes being relatively small), together, the identified markers can achieve a satisfactory classification (e.g., 100 percent sensitivity and >91 percent specificity).

Proteomic Expression Profiling Markers ("Proteomic Markers")

Exemplary peptide sequences comprising one or more proteomic markers that can be used to determine the acute rejection status of a heart transplant in a subject are provided in Table 4. These peptides were produced by a tryptic digest (as described herein) and identified in the iTRAQ experiments. Detection of one or more than one peptide in a sample is indicative of the proteomic marker being present in the sample. While iTRAQ was one exemplary method used to detect the peptides, other methods described herein, for example immunological based methods such as ELISA may also be useful. Alternately, specific antibodies may be raised against the one or more proteins, isoforms, precursors, polypeptides, peptides, or portions or fragments thereof, and the specific antibody used to detect the presence of the one or more proteomic marker in the sample. Methods of selecting suiTablepeptides, immunizing animals (e.g. mice, rabbits or the like) for the production of antisera and/or production and screening of hybridomas for production of monoclonal antibodies are known in the art, and described in the references disclosed herein.

Assays for determining the acute rejection status of a heart transplant using the panels of proteomic markers of the invention may have a sensitivity of at least 80%, at least 85%, 90%, at least 91%, at least 92%, at least 93%, at least 94%, at least 95%, at least 96%, at least 97%, at least 98%, at least 99%, or 100%; a specificity of at least 40%, at least 41%, at least 42%, at least 43%, at least 45%, at least 48%, at least 50%, at least 55%, at least 60%, at least 70%, at least 80%, at least 90%, at least 91%, at least 92%, at least 93%, at least 95%, at least 96%, at least 97%, at least 98%, at least 99%, or 100%; a PPV of at least 2%, at least 5%, or at least 7%; and a NPV of at least 95%, at least 96%, at least 97%, at least 98%, at least 99%, or 100%.

The invention also provides for a kit for use in predicting or diagnosing a subject's rejection status. The kit may comprise reagents for specific and quantitative detection of at least one, two, three, four, five, or six of the proteomic markers in Table 4, along with instructions for the use of such reagents and methods for analyzing the resulting data. For example, the kit may comprise antibodies or fragments thereof, specific for the proteomic markers (primary antibodies), along with one or more secondary antibodies that may incorporate a detectable label; such antibodies may be used in an assay such as an ELISA. Alternately, the antibodies or fragments thereof may be fixed to a solid surface, e.g. an antibody array. The kit may be used alone for predicting or diagnosing a subject's rejection status, or it may be used in conjunction with other methods for determining clinical variables, or other assays that may be deemed appropriate. Instructions or other information useful to combine the kit results with those of other assays to provide a non-rejection cutoff index for the prediction or diagnosis of a subject's rejection status may also be provided.

Biomarker Panels Comprising Both Nucleic Acid Markers and Proteomic Markers

The invention also provides a biomarker panel that comprises at least one nucleic acid markers selected from Tables 3, 5 or 7, and at least one proteomic marker selected from Table 4. Assays for determining the acute rejection status of a heart transplant using panels comprising both proteomic markers and nucleic acid markers of the invention have a sensitivity of at least 80%, at least 85%, at least 90%, at least 91%, at least 92%, at least 93%, at least 94%, at least 95%, at least 96%, at least 97%, at least 98%, at least 99%, or 100%; a specificity of at least 60%, at least 65%, at least 70%, at least 75%, at least 80%, at least 85%, at least 88%, at least 90%, at least 91%, at least 92%, at least 93%, at least 95%, at least 96%, at least 97%, at least 98%, at least 99%, or 100%; a PPV of at least 5%, at least 10%, at least 15%, at least 20%, at least 25%, at least 30%; or at least 32%; and a NPV of at least 95%, at least 96%, at least 97%, at least 98%, at least 99%, or 100%.

Methods for selecting and manufacturing such antibodies, as well as their inclusion on a 'chip' or an array, or in an assay, and methods of using such chips, arrays or assays are referenced or described herein.

RNA Extraction and Microarray Analysis

Subjects were enrolled according to Biomarkers in Transplantation standard operating procedures. Subjects waiting for a cardiac transplant at the St. Paul's Hospital, Vancouver, BC were approached by the research coordinators and consented subjects were enrolled in the study. All heart transplants are overseen by the British Columbia Transplant (BCT) and all subjects receive standard immunosuppressive therapy consisting of cyclosporine, prednisone and mycophenolate mofetil. Cyclosporine was replaced by tacrolimus for women and by sirolimus in cases of renal impairment. Blood samples from consented subjects were taken before transplant (baseline) and collected in PAXGene tubes, placed in an ice bath for delivery, frozen at $-20°$ C. for one day and then stored at $-80°$ C. until RNA extraction for nucleic acid marker analysis.

RNA extraction was performed on thawed samples using the PAXgene™ Blood RNA Kit [Cat #762134] to isolate total RNA. Between 4 and 10 micro g of RNA was routinely isolated from 2.5 ml whole blood and the RNA quality confirmed using the Agilent BioAnalyzer. Samples with 1.5 micro g of RNA, an RIN number >5, and A240/A280>1.9 were packaged on dry ice and shipped by Federal Express to the Microarray Core (MAC) Laboratory, Children's Hospital, Los Angeles, Calif. for Affymetrix microarray analysis. The microarray analysis was performed by a single technician at the CAP/CLIA accredited MAC laboratory. Nascent RNA was used for double stranded cDNA synthesis. The cDNA was then labeled with biotin, fragmented, mixed with hybridization cocktail and hybridized onto GeneChip Human Genome U133 Plus 2.0 Arrays. The arrays were scanned with the Affymetrix System in batches of 48 with an internal RNA control made from pooled normal whole blood. Microarrays were checked for quality issues using Affymetrix version 1.16.0 and affyPLM version 1.14.0 BioConductor packages (Bolstad, B., Low Level Analysis of High-density Oligonucleotide Array Data: Background, Normalization and Summarization. 2004, University of California, Berkeley; Irizarry et al. 2003. Biostatistics 4(2): 249-64). The arrays with lower quality were repeated with a different RNA aliquot from the same time point. The Affymetrix™ NetAffx™ Annotation database Update Release 25 (March 2008) was used for identification and analysis of microarray results.

The expression profile of nucleic acid markers can also be confirmed by RT-PCR or NanoString nCounter technology, The expression of these markers can also be detected and validated using more clinically-amenable technologies, e.g., the HTG Molecular qNPA (quantitative nuclease protection assay) platform. The HTG Edge System is a desired platform for clinical assay development because it is fully-automated, which greatly simplifies laboratory workflow, requires small sample input and minimal hands-on time.

One or more housekeeping genes can be used in these assay platforms, for example, ACTB, ANT, B2M, OAZ1, RPL11, or SDHA.

Proteomic Expression Analysis

For protein expression studies, blood samples were collected prior to transplant and serially for up to 3 years post-transplant, and at times of suspected rejection. Pre-transplant and protocol heart tissue biopsies were collected and placed directly into RNAlater™ Tissue Protect Tubes and stored at −80° C. The biopsies were blindedly reviewed by multiple experienced cardiac pathologists and classified according to the current ISHLT grading scale. Patients with rejection grade >2R were identified as having AR for purposes of this investigation. Such patients received appropriate treatments for acute rejection.

Sample Processing

Blood samples were collected in EDTA tubes, immediately stored on ice. Plasma was obtained within 2 hours from each whole blood sample by centrifugation, aliquoted and stored at −80 degrees centigrade Peripheral blood plasma drawn from 16 healthy individuals was pooled, aliquoted and stored at −70 degrees centigrade. Heart transplant patient samples were immediately stored on ice before processing and storage at −70 degrees centigrade within 2 hours. All blood was drawn into tubes with EDTA as an anti-coagulant (BD Biosciences; Franklin Lakes, N.J.). Each plasma sample was then thawed to room temperature, diluted 5 times with 10 mM phosphate buffered saline (PBS) at pH 7.6, and filtered with spin-X centrifuge tube filters (Millipore). Diluted plasma was injected via a 325 micro L sample loop onto a 5 niL avian antibody affinity column (Genway Biotech; San Diego, Calif.) to remove the 14 most abundant plasma proteins: albumin, fibrinogen, transferin, IgG, IgA, IgM, haptoglobin, a2-macroglobulin, al-acid glycoprotein, al-antitrypsin, Apoliprotein-I, Apoliprotein-II, complement C3 and Apoliprotein B). Flow-through fractions were collected and precipitated by adding TCA to a final concentration of 10 percent and incubated at 4 degrees centigrade for 16-18 hours. The protein precipitate was recovered by centrifugation 3200 g at 4 degrees centigrade for 1 hour, washed three times with ice cold acetone (EMD; Gibbstown, N.J.) and re-hydrated with 200-300 micro L iTRAQ buffer consisting of 45:45:10 saturated urea (J. T. Baker; Phillipsburg, N.J.), 0.05 M TEAB buffer (Sigma-Aldrich; St Louis, Mo.), and 0.5 percent SDS (Sigma-Aldrich; St Louis, Mo.). Each sample was then stored at −70 degrees centigrade. Samples of depleted plasma protein, 100 mg, were digested with sequencing grade modified trypsin (Promega Madison, Wis.) and labeled with iTRAQ reagents according to manufacturer's protocol (Applied Biosystems; Foster City, Calif.). To ensure interpretable results across different runs, a common reference sample was processed together with 3 patient samples in all runs. The reference sample consisted of a pool of plasma from 16 healthy individuals and was consistently labeled with iTRAQ reagent 114. Patient samples were randomly labeled with iTRAQ reagents 115, 116 and 117. iTRAQ labeled peptides were then pooled and acidified to pH 2.5-3.0. and separated first by strong cation exchange chromatography (PoIyLC Inc., Columbia, Md. USA), followed by reverse phase chromatography (Michrom Bioresources Inc., Auburn, Calif. USA) and spotted directly onto 384 spot MALDI ABI 4800 plates, 4 plates per experiment, using a Probot microfraction collector (LC Packings, Amsterdam, Netherlands).

Trypsin Digest and iTRAQ Labeling

Total protein concentration was determined using the bicinchoninic acid assay (BCA) (Sigma-Aldrich, St Louis, Mo. USA) and 100 micro g of total protein from each sample was precipitated by the addition of 10 volumes of HPLC grade acetone at −20 degrees centigrade (Sigma-Aldrich, Seelze, Germany) and incubated for 16-18 hours at −20 degrees centigrade The protein precipitate was recovered by centrifugation at 16 110×g for 10 min and solubilized in 50 mM TEAB buffer (Sigma-Aldrich; St Louis, Mo.) and 0.2 percent electrophoresis grade SDS (Fisher Scientific; Fair Lawn, N.J.). Proteins in each sample were reduced with TCEP (Sigma-Aldrich; St Louis, Mo.) at 3.3 mM and incubated at 60 degrees centigrade for 60 min. Cysteines were blocked with methyl methane thiosulfonate at a final concentration of 6.7 mM and incubated at room temperature for 10 min.

Reduced and blocked samples were digested with sequencing grade modified trypsin (Promega Madison, Wis.) and incubated at 37 degrees centigrade for 16-18 hours. Trypsin digested peptide samples were dried in a speed vacuum (Thermo Savant; Holbrook, N.Y.) and labeled with iTRAQ reagent according to the manufacturer's protocol (Applied Biosystems; Foster City, Calif.). Labeled samples were pooled and acidified to pH 2.5-3.0 with concentrated phosphoric acid (ACP Chemicals Inc; Montreal, QC, Canada).

2D-LC Chromatography iTRAQ labeled peptide were separated by strong cation exchange chromatography (SCX) using a 4.6 mm internal diameter (ID) and 100 mm in length Polysulphoethyl A column packed with 5 micro m beads with 300 A pores (PoIyLC Inc., Columbia, Md. USA) on a VISION workstation (Applied Biosystems; Foster City, Calif.). Mobile phases used were Buffer A composed of 10 mM monobasic potassium phosphate (Sigma-Aldrich; St Louis, Mo.) and 25 percent acetonitrile (EMD Chemicals; Gibbstown, N.J.) pH 2.7, and Buffer B that was the same as A except for the addition of 0.5 M potassium chloride (Sigma-Aldrich St Louis, Mo., USA). Fractions of 500 micro L were collected over an 80 minute gradient divided into two linear profiles: 1) 0-30 min with 5 percent to 35 percent of Buffer B, and 2) 30-80 min with 35 percent to 100 percent of Buffer B. The 20 to 30 fractions with the highest level of peptides, detected by UV trace, were selected and the volume reduced to 150 micro L pre fraction. Peptides were desalted by loading fractions onto a Cl 8 PepMap guard column (300 micro m ID×5 mm, 5 micro m, 100 A, LC Packings, Amsterdam) and washing for 15 min at 50 micro L/min with mobile phase A consisting of water/acetonitrile/TFA 98:2:0.1 (v/v). The trapping column was then switched into the nano flow stream at 200 nL/min where peptides were loaded onto a Magic Cl 8 nano LC column (15 cm, 5 micro m pore size, 100 A, Michrom Bioresources Inc., Auburn Calif., USA) for high resolution chromatography. Peptides were eluted by the following gradient: 0-45 min with 5 percent to 15 percent B (acetonitrile/water/TFA 98:2:0.1, v/v); 45-100 min with 15 percent to 40 percent B, and 100-105 min with 40 percent to 75 percent B. The eluent was spotted directly onto 96 spot MALDI ABI 4800 plates, 4 plates per experiment, using a Probot microfration collector (LC Packings, Amsterdam, Netherlands). Matrix solution, 3 mg/mL a-cyano-4-hydroxy-cinnamic acid (Sigma-Aldrich, St Louis, Mo. USA) in 50 percent ACN, 0.1 percent TFA, was then added at 0.75 micro L per spot.

Mass Spectrometry and Data Processing

Peptides spotted onto MALDI plates were analyzed by a 4800 MALDI TOF/TOF analyzer (Applied Biosystems;

Foster City, Calif.) controlled using 4000 series Explorer version 3.5 software. The mass spectrometer was set in the positive ion mode with an MS/MS collision energy of 1 keV. A maximum of 1400 shots/spectrum were collected for each MS/MS run causing the total mass time to range from 35 to 40 hours. Peptide identification and quantitation was carried out by ProteinPilot™ Software v2.0 (Applied Biosystems/ MDS Sciex, Foster City, Calif. USA) with the integrated new Paragon™ Search Algorithm (Applied Biosystems) (Shilov et al., 2007) and Pro Group™ Algorithm. Database searching was performed against the international protein index (IPI HUMAN v3.39) (Kersey et al, 2004). The precursor tolerance was set to 150 ppm and the iTRAQ fragment tolerance was set to 0.2 Da. Identification parameters were set for trypsin cleavages, cysteine alkylation by MMTS, with special factors set at urea denaturation and an ID focus on biological modifications. The detected protein threshold was set at 85 percent confidence interval.

Pro Group™ Algorithm (Applied Biosystems) assembled the peptide evidence from the Paragon™ Algorithm into a comprehensive summary of the proteins in the sample and organized the set of identified proteins in protein groups to maintain minimal lists of protein identities within each iTRAQ run. The relative protein levels (protein ratios of concentrations of labels 115, 116 and 117 relative to label 114, respectively) were estimated by Protein Pilot using the corresponding peptide ratios (including singleton peaks). The average protein ratios were calculated by ProteinPilot based on a weighted average of the log ratios of the individual peptides for each protein. The weight of each log ratio was the inverse of the Error Factor, an estimate of the error in the quantitation, calculated by Pro Group Algorithm. This weighted average were then converted back into the linear space and corrected for experimental bias using the Auto Bias correction option in Pro Group Algorithm. Peptide ratios coming from the following cases were excluded from the calculation of the corresponding average protein ratios: shared peptides (i.e., the same peptide sequence was claimed by more than one protein), peptides with a precursor overlap (i.e., the spectrum yielding the identified peptide was also claimed by a different protein but with an unrelated peptide sequence), peptides with a low confidence (i.e., peptide ID confidence <1.0 percent), peptides that did not have an iTRAQ modification, peptides with only one member of the reagent pair identified, and peptide ratios where the sum of the signal-to-noise ratio for all of the peak pairs was less than 9. Further information on these and other quantitative measures assigned to each protein and on the bias correction are given in ProteinPilot Software documentation.

Statistical Analysis

Applying a plurality of mathematical and/or statistical analytical methods to a microarray dataset may indicate varying subsets of significant markers, leading to uncertainty as to which method is 'best' or 'more accurate'. Regardless of the mathematics, the underlying biology is the same in a dataset. By applying a plurality of mathematical and/or statistical methods to a microarray dataset or the mass spectrometry dataset and assessing the statistically significant subsets of each for common markers to all, the uncertainty is reduced, and clinically relevant core group of markers is identified.

Exemplar statistical models that can be used include a robust moderated t-test (eBayes—Smyth G K) for the evaluation of differential protein expression levels, and linear models and empirical Bayes methods for assessing differential expression in microarray experiments. StatAppl Genet Mol Biol. 2004; 3:Article3 (Berkeley Electronic Press).

Classification methods such as elaticnet, random forest, Linear Discriminant Analysis (LDA), regression, and others were applied to identify a subset of the markers to be included in the mRNA and protein panel Various parameters are employed to evaluate the performance of panels of biomarkers used in determining acute rejection status in patients. AUC, "area under the curve", which is examined within the scope of ROC (receiver-operator characteristic) analysis and which is a measure of the quality of the individual parameter (biomarker) or a combination of biomarkers, based on the cases examined. Thus, the sensitivity on the ordinate is plotted against specificity on the abscissa in the diagram. Specificity is defined as the number of actually negative samples divided by the sum of the numbers of the actually negative and false positive samples. A specificity of 1 means that a test recognizes all acute rejectors as acute rejectors, i.e., no non-rejector is identified as being an acute rejector. This says nothing about how reliably the test recognizes acute rejectors. Sensitivity is defined as the number of actually acute rejectors divided by the sum of the numbers of the actually acute rejecters and the number of non rejectors that has been false diagnosed as acute rejectors. A sensitivity of 1 means that the test recognizes all acute rejectors. This says nothing about how reliably the test recognizes non-rejectors. Thus, an AUC value of 1 means that all samples have been assigned correctly (specificity and sensitivity of 1), an AUC value of 0.5 means that the samples have been assigned with guesswork probability and the parameter thus has no significance.

In a preferred embodiment of the invention, the panel of biomarkers employed to determine the acute rejection status in patients—whether it is a panel of nucleic acid markers, or a panel of proteomic markers, or a panel of combination of nucleic acid and protein markers—has an AUC value that is greater than 0.6, preferably greater than 0.7. In another preferred embodiment of the invention, the sensitivity of the panels is equal to or greater than 91%, and the specificity of the panels is equal to or greater than 15%.

"Positive predictive value" or "PPV" is calculated by TP/(TP+FP) or the true positive fraction of all positive test results. It is inherently impacted by the prevalence of the disease and pre-test probability of the population intended to be tested. "Negative predictive value" or "NPV" is calculated by TN/(TN+FN) or the true negative fraction of all negative test results. It also is inherently impacted by the prevalence of the disease and pre-test probability of the population intended to be tested. In one preferred embodiment of the invention, the PPV of the panels of markers used to determine the acute rejection status in patients is equal to or greater than 4% and the NPV of the panels is equal to or greater than 98%.

The present invention is described by reference to the following Examples, which are offered by way of illustration and are not intended to limit the invention in any manner. Standard techniques well known in the art or the techniques specifically described below were utilized.

EXAMPLES

Example 1. Nucleic Acid and Protein Markers for Diagnosing Transplant Rejection

The development of the biomarker panel in determining the acute rejection status of a patient involves three phases:

a biomarker discovery phase, a biomarker replication phase, and an assay migration and validation phase. In the biomarker discovery phase: 65 heart transplant patients were recruited from a single site (Vancouver, Canada). Nucleic acid expression of over 36,000 nucleic acid markers were analyzed using Affymetrix microarrays, HTG EdgeSeq, and NanoString nCounter technology. Over 200 proteomic markers in plasma were analyzed using mass spectrometry and ELISA. Panels of nucleic acid markers or proteomic markers with an area under the receiver operating characteristics curve (AUC) above 0.8 were moved to the biomarker replication phase.

In the biomarker replication phase: 84 heart transplant patients were recruited from eight enrolling sites across Canada. Nucleic acid expression and proteomic expression were performed on the markers identified in the discovery phase with the same technologies. Over 99% negative predictive value (NPV) was achieved for panels of nucleic acid markers and panels of proteomic panels. The best performing panels were selected for development in the assay migration and validation phase.

In the assay migration and validation phase, panels of markers identified in previous phases were migrated to clinically-amenable technologies, e.g., the HTG Molecular qNPA (quantitative nuclease protection assay) platform for detection of nucleic acid expression. The HTG Edge System is a desired platform for clinical assay development because it is fully-automated, which greatly simplifies laboratory workflow; and it requires small sample input and minimal hands-on time. Over 100 patients (and 350 samples) were collected through the 8 pan-Canadian sites for testing in this stage, in which 40 mRNA markers (Table 3) were tested. See Table 3. In the initial testing on the multiplex HTG study, a panel of 10 mRNA markers (Table 5) was identified and its performance in determining the acute rejection status is discussed in Example 2. The mRNA markers identified herein participate in a range of biological processes: cellular and humoral immune responses, acute phase inflammatory pathways, proliferation, chemotaxis, development, cell adhesion, apoptosis, signal transduction, cell cycle, and reproduction. See FIG. 1.

Figure 2:
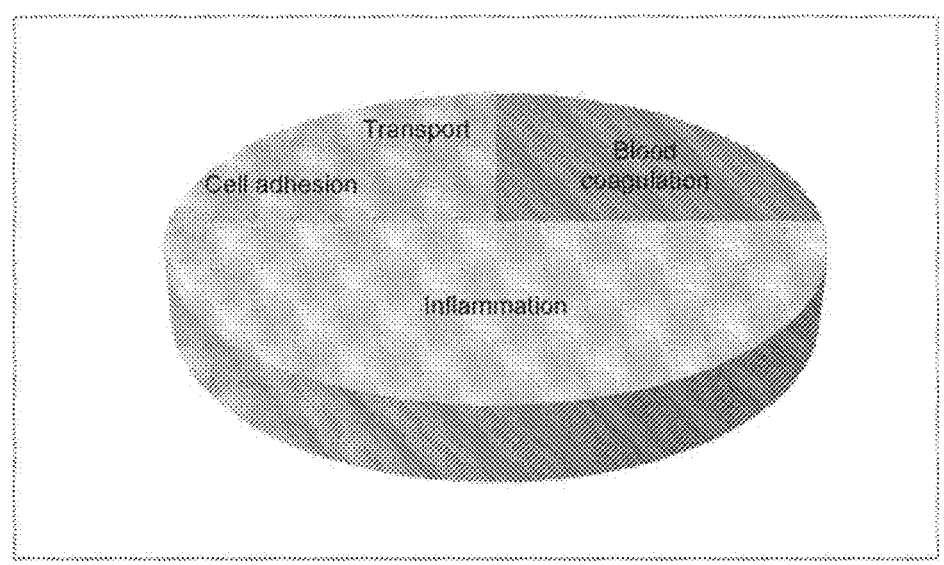
FIG. 2 shows a range of biological processes in which the proteomic markers disclosed herein participate.

Six proteomic markers (Table 4), originally identified by MS technologies, were also confirmed by immunoassays (ELISAs) to be suitable as markers for determining the acute rejection status. The performance of the protein panel comprising these six proteomic markers is described in Example 2. These proteomic markers participate in a range of biological processes, including cell adhesion, transport, blood coagulation, and inflammation. See FIG. 2. These proteomic markers, along with housekeeping genes, will be migrated onto a multiplexed, immuno-based microfluidics point-of-care platform for further testing and validation.

TABLE 3

| 40 nucleic acid markers. | |
|---|---|
| Symbol | Gene Name |
| CD177 | CD177 molecule |
| CPA3 | carboxypeptidase A3 (mast cell) |
| HEBP1 | heme binding protein 1 |
| ORM1 | orosomucoid 1 |
| VNN1 | vanin 1 |
| CNTNAP3 | contactin associated protein-like 3 |
| ADD2 | adducin 2 (beta) |
| AKAP12 | A kinase (PRKA) anchor protein 12 |
| APOBEC3C | apolipoprotein B mRNA editing enzyme, catalytic polypeptide-like 3C |

TABLE 3-continued

| 40 nucleic acid markers. | |
|---|---|
| Symbol | Gene Name |
| CTSE | cathepsin E |
| KEL | Kell blood groUp, metallo-endopeptidase |
| LTB | lymphotoxin-beta isoform a |
| RNF5 | ring finger protein 5 |
| UBL7 | ubiquitin-like 7 (bone marrow stromal cell-derived) |
| HCLS1 | hematopoietic cell-specific Lyn substrate 1 |
| PSTPIP1 | proline-serine-threonine phosphatase interacting protein 1 |
| ENO1 | BH3 interacting domain death agonist |
| IL16 | Interleukin 16 (lymphocyte chemoattractant factor) |
| LOC284454 | Hypothetical protein LOC284454 |
| RAB37 | RAB37, member RAS oncogene family |
| TIMP1 | TIMP metallopeptidase inhibitor 1 |
| C3 | complement component 3 |
| CD44 | CD44 molecule (Indian blood group) |
| FCER1G | Fc fragment of IgE, high affinity I, receptor for; gamma polypeptide |
| IFIT2 | interferon-induced protein with tetratricopeptide repeats 2 |
| IKZF1 | IKAROS family zinc finger 1 (Ikaros) |
| IL4R | interleukin 4 receptor |
| LILRA5 | leukocyte immunoglobulin-like receptor, subfamily A (with TM domain), member 5 |
| NFKB1 | nuclear factor of kappa light polypeptide gene enhancer in B-cells 1 |
| SERPING1 | serpin peptidase inhibitor, clade G (C1 inhibitor), member 1 |
| SOCS3 | suppressor of cytokine signaling 3 |
| STAT5B | signal transducer and activator of transcription 5B |
| BTK | Bruton agammaglobulinemia tyrosine kinase |
| CD99 | CD99 molecule |
| CTNNB1 | catenin (cadherin-associated protein), beta 1, 88 kDa |
| IRF7 | interferon regulatory factor 7 |
| LTBR | Lymphotoxin Beta Receptor |
| NFKBIZ | nuclear factor of kappa light polypeptide gene enhancer in B-cells inhibitor, zeta |
| STAT5A | signal transducer and activator of transcription 5A |
| SYK | spleen tyrosine kinase |
| Symbol | Protein Name |
| FXIII | Factor XIII |
| FV | Factor V |
| CFI | Complement factor I |
| ADP | Adiponectin |
| PLTP | Phospholipid transfer protein |
| PROCR | Endothelial protein C receptor |

TABLE 4

| Proteomics markers. | |
|---|---|
| FXIII | Factor XIII |
| FV | Factor V |
| CFI | Complement factor I |
| ADP | Adiponectin |
| PLTP | Phospholipid transfer protein |
| PROCR | Endothelial protein C receptor |

Example 2. Initial Biomarker Performance on HTG mRNA Assay and ELISA 37 banked samples were used in the initial assay migration and validation phase study. 14 of them were previously diagnosed with acute rejection status (AR), and 23 with no rejection status (NR). The panel of 10 nucleic acid markers in Table 5 was assayed using the multiplex HTG mRNA assay and the panel of six proteomic markers in Table 4 were assayed using ELISA kits.

TABLE 5

10 nucleic acid markers.

| | |
|---|---|
| HEBP1 | Heme binding protein 1 |
| ORM1 | Orosomucoid 1 |
| IL4R | Interleukin 4 receptor |
| CD44 | CD44 molecule (Indian blood group) |
| SERPING1 | serpin peptidase inhibitor, clade G (C1 inhibitor), member 1 |
| FCER1G | Fc fragment of IgE, high affinity I, receptor for; gamma polypeptide |
| C3 | complement component 3 |
| NFKB1 | nuclear factor of kappa light polypeptide gene enhancer in B-cells 1 |
| LTBR | Lymphotoxin Beta Receptor |
| BTK | Bruton agammaglobulinemia tyrosine kinase |

The results show that the assay, which employs a panel comprising the 10 nucleic acid markers to determine the acute rejection status in a patient, had a sensitivity of 100%, a specificity of 74%. This indicates that by using only 10 mRNA measurements on the HTG assay, those samples from patients without acute rejection, i.e. non rejectors (NR) and moderate rejectors (MR), can be identified 100% of the time; and samples from patients who had acute rejection, i.e. acute rejectors, can be identified 74% of the time. The assay using the panel showed a positive predictive value (PPV) of 14%, a negative predictive value (NPV) of 100%, and an AUC of 0.85. The panel comprising the six proteomic markers had a sensitivity of 100% and a specificity of 48%. The PPV for the panel was 7%, and NPV was 100%. The AUC for the panel was 0.62. The result also shows that the a biomarker panel combining the 6 proteomic markers and the 10 nucleic acid markers through computational methods improved the specificity of the HTG assay using the 10 nucleic acid markers alone, from 74% to 91%. See Table 6.

TABLE 6

Performance of the diagnostic biomarker panels.

| Panel | sensitivity | Specificity | PPV | NPV | AUC |
|---|---|---|---|---|---|
| 10 mRNAs | 100% | 74% | 14% | 100% | 0.85 |
| 6 proteins | 100% | 48% | 7% | 100% | 0.62 |
| combined | 100% | 91% | 32% | 100% | 0.91 |

Example 3. Initial Biomarker Performance on Nanostring nCounter

A panel consisting of the 6 nucleic acid markers in Table 7 was tested in two different cohorts using the NanoString nCounter technology. The first is the recalibration cohort, in which the 6 nucleic acid marker panel was tested on samples from 38 subjects. 15 subjects had acute rejection and 23 had no rejection or moderate rejection to heart transplant. The second is the replication cohort, in which the panel of the 6 nucleic acid makers was tested on samples from 126 subjects, of which 22 had acute rejection and 104 had no rejection or moderate rejection.

The results (Table 8) show that the assay used in the recalibration cohort had a sensitivity of 100%, a specificity of 22%, a PPV of 5%, and a NPV of 100%. The assay used in the replication cohort had a sensitivity of 91%, a specificity of 15%, a PPV of 4%, and a NPV of 98%.

TABLE 7

6 nucleic acid markers.

| Gene Symbol | Gene name |
|---|---|
| HEBP1 | Heme binding protein 1 |
| CD 177 | CD 177 molecule |
| CPA3 | Carboxypeptidase A3 (Mast Cell) |
| VNN1 | Vanin 1 |
| ORM1 | Orosomucoid 1 |
| CNTNAP3 | Contactin associated protein-like 3 |

TABLE 8

The performance of the 6 nucleic acid markers.

| Panel | Cohort | Sensitivity | Specificity | PPV | NPV |
|---|---|---|---|---|---|
| 6 mRNAs | Recalibration | 100% | 22% | 5% | 100% |
| | Replication | 91% | 15% | 4% | 98% |

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A method of determining the acute cellular rejection status of a heart transplant in a subject using a biomarker panel comprising nucleic acid markers, the method comprising the steps of:
   a. determining the nucleic acid expression profile of the nucleic acid markers in a biological sample from the subject, wherein the biomarker panel comprises nucleic acid markers CD177, CPA3, HEBP1, ORM1, VNN1, CNTNAP3, AKAP12, CTSE, and IFIT2, and the housekeeping genes ACTB, B2M, and OAZ1,
   b. comparing a concentration of the nucleic acid markers to a control value, wherein the control value is a concentration of the corresponding nucleic acid markers in a biological sample from a healthy control subject,
   c. determining whether the concentration of the nucleic acid markers in the biological sample from the subject is increased or decreased relative to the control value, and
   selecting a subject who has a higher concentration of the nucleic acid markers relative to the control value, categorizing the subject as having acute cellular rejection status and performing a biopsy on the subject.

2. The method of claim 1, wherein the nucleic acid expression profile is determined by NanoString nCounter technology.

3. The method of claim 1, wherein the biological sample is obtained from the subject weekly, biweekly, monthly, and bimonthly following the heart transplant.

4. The method of claim 1, wherein the subject has a International Society for Heart and Lung Transplantation (ISHLT) grade that is 2R or higher.

* * * * *